US012779026B2

(12) United States Patent
Amara et al.

(10) Patent No.: US 12,779,026 B2
(45) Date of Patent: Nov. 3, 2026

(54) HIV IMMUNOGENS, VACCINES, AND METHODS RELATED THERETO

(71) Applicant: Emory University, Atlanta, GA (US)

(72) Inventors: Rama Rao Amara, Atlanta, GA (US); Sailaja Gangadhara, Atlanta, GA (US); Anusmita Sahoo, Atlanta, GA (US); Tiffany Turner-Styles, Atlanta, GA (US)

(73) Assignee: Emory University, Atlanta, GA (US)

( * ) Notice: Subject to any disclaimer, the term of this patent is extended or adjusted under 35 U.S.C. 154(b) by 938 days.

(21) Appl. No.: 17/776,896

(22) PCT Filed: Nov. 13, 2020

(86) PCT No.: PCT/US2020/060472
§ 371 (c)(1),
(2) Date: May 13, 2022

(87) PCT Pub. No.: WO2021/097254
PCT Pub. Date: May 20, 2021

(65) Prior Publication Data

US 2022/0401546 A1 Dec. 22, 2022

Related U.S. Application Data

(60) Provisional application No. 62/935,142, filed on Nov. 14, 2019.

(51) Int. Cl.
*A61K 39/12* (2006.01)
*A61P 31/18* (2006.01)
(Continued)

(52) U.S. Cl.
CPC .............. *A61K 39/12* (2013.01); *A61P 31/18* (2018.01); *C07K 14/005* (2013.01); (Continued)

(58) Field of Classification Search
None
See application file for complete search history.

(56) References Cited

U.S. PATENT DOCUMENTS 10,307,478 B2 6/2019 Harrison
2014/0335126 A1 11/2014 Haynes
(Continued)

FOREIGN PATENT DOCUMENTS

WO WO-2013039792 A1 * 3/2013 ............. A61K 39/12
WO 2013085550 6/2013
(Continued)

OTHER PUBLICATIONS

SEQ 3 pairwise with dots alignment with GenBank Access No. AAT67547.1 NCBI Blast_Protein Sequence completed May 21, 2025.*

(Continued)

*Primary Examiner* — Shanon A. Foley
(74) *Attorney, Agent, or Firm* — Emory Patent Group

(57) ABSTRACT

This disclosure relates to HIV envelope proteins or envelope protein fragments, or trimeric complexes thereof which have uses in vaccination methods or therapeutic strategies. In certain embodiments, this disclosure relates to HIV envelope proteins or envelope protein fragments, or trimeric complexes thereof, comprising an arginine (R) at position 166, glutamine (Q) at position 170, and an amino acid histidine (H) at position 173. In certain embodiments, this disclosure relates to nucleic acids and recombinant vectors encoding said proteins.

15 Claims, 5 Drawing Sheets

Specification includes a Sequence Listing.

(51) Int. Cl.
*C07K 14/005* (2006.01)
*A61K 39/00* (2006.01)

(52) U.S. Cl.
CPC .............. *A61K 2039/55577* (2013.01); *C12N 2740/16023* (2013.01); *C12N 2740/16122* (2013.01); *C12N 2740/16134* (2013.01)

(56) References Cited

U.S. PATENT DOCUMENTS

| | | | | |
|---|---|---|---|---|
| 2015/0283227 | A1 | 10/2015 | Haynes | |
| 2016/0243215 | A1 | 8/2016 | Barouch | |
| 2018/0072777 | A1 | 3/2018 | Rutten | |
| 2019/0330279 | A1 | 10/2019 | Kwong | |
| 2020/0165303 | A1 | 5/2020 | Kong | |
| 2020/0230229 | A1 | 7/2020 | Kwong | |
| 2022/0401546 | A1* | 12/2022 | Amara | C07K 14/005 |

FOREIGN PATENT DOCUMENTS

| | | | |
|---|---|---|---|
| WO | 2015051270 | 4/2015 | |
| WO | WO-2016037154 A1 * | 3/2016 | A61K 39/12 |
| WO | 2018075559 | 4/2018 | |
| WO | 2019152746 | 8/2019 | |

OTHER PUBLICATIONS

Abrahams et al. Quantitating the Multiplicity of Infection with Human Immunodeficiency Virus Type 1 Subtype C Reveals a Non-Poisson Distribution of Transmitted Variants, Journal of Virology, 2009, 3556-3567.
Burton et al. Clade C HIV-1 Envelope Vaccination Regimens Differ in Their Ability to Elicit Antibodies with Moderate Neutralization Breadth against Genetically Diverse Tier 2 HIV-1 Envelope Variants, J Virol, 2019, 93:e01846-18.
Churchill, HIV reservoirs: what, where and how to target them, Nature Reviews, 2016, vol. 14, 55-60.
Gao et al. Advances in HIV-1 Vaccine Development, Viruses, 2018, 10, 167, 26 pages.
He et al. HIV-1 vaccine design through minimizing envelope metastability, Sci Adv, 2018, 4(11):eaau6769.
Jones et al. A Trimeric HIV-1 Envelope gp120 Immunogen Induces Potent and Broad Anti-V1V2 Loop Antibodies against HIV-1 in Rabbits and Rhesus Macaques, J Virol, 2018, 92:e01796-17.
Julien et al. Crystal structure of a soluble cleaved HIV-1 envelope trimer, Science. 2013, 342(6165).
Kong et al. Uncleaved prefusion-optimized gp140 trimers derived from analysis of HIV-1 envelope metastability, Nat Commun, 2016, 7:12040.
Kwon et al. Crystal structure, conformational fixation, and entry-related interactions of mature ligand-free HIV-1 Env, Nat Struct Mol Biol. 2015, 22(7): 522-531.
Robb et al. Ad hoc analysis of behavior and time as co-variates of the Thai phase III efficacy trial: RV 144, Lancet Infect Dis. 2012, 12(7): 531-537.
Rodenburg et al. Near Full-Length Clones and Reference Sequences for Subtype C Isolates of HIV Type 1 from Three Different Continents, Aids Research and Human Retroviruses vol. 17, No. 2, 2001, pp. 161-168.
Sahoo et al. Structure-guided changes at the V2 apex of HIV-1 clade C trimer enhance elicitation of autologous neutralizing and broad V1V2-scaffold antibodies, Cell Rep. 2022, 38(9): 110436.
Sanders et al. A Next-Generation Cleaved, Soluble HIV-1 Env Trimer, BG505 SOSIP.664 gp140, Expresses Multiple Epitopes for Broadly Neutralizing but Not Non-Neutralizing Antibodies, PLoS Pathog, 2013, 9(9): e1003618.
Sharma et al. Cleavage-Independent HIV-1 Env Trimers Engineered as Soluble Native Spike Mimetics for Vaccine Design, Cell Reports 11, 539-550, 2015.
Smith et al. Comparative Immunogenicity of HIV-1 Clade C Envelope Proteins for Prime/Boost Studies, PLoS ONE, 2010, 5(8): e12076.
Styles et al. Human Immunodeficiency Virus C.1086 Envelope gp140 Protein Boosts following DNA/Modified Vaccinia Virus Ankara Vaccination Fail to Enhance Heterologous Anti-V1V2 Antibody Response and Protection against Clade C Simian-Human Immunodeficiency Virus Challenge, J Virol, 2019, 93:e00934-19.
Wilmschen et al. Viral Vectors for the Induction of Broadly Neutralizing Antibodies against HIV, Vaccines, 2019, 7, 119.

* cited by examiner

HIV IMMUNOGENS, VACCINES, AND METHODS RELATED THERETO

CROSS-REFERENCE TO RELATED APPLICATIONS

This application is the National Stage of International Application No. PCT/US2020/060472 filed Nov. 13, 2020, which claims the benefit of U.S. Provisional Application No. 62/935,142 filed Nov. 14, 2019. The entirety of each of these applications is hereby incorporated by reference for all purposes.

STATEMENT REGARDING FEDERALLY SPONSORED RESEARCH OR DEVELOPMENT

This invention was made with government support under AI109633 awarded by the National Institutes for Health. The government has certain rights in this invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 20038PCT_ST25.txt. The text file is 20 KB, was created on Nov. 13, 2020, and is being submitted electronically via EFS-Web.

BACKGROUND

There are millions of humans living with HIV/AIDS. Combination antiretroviral therapy (cART) treatment regimens have successfully prolonged the lives of infected individuals. However, there is a need to develop a safe and effective HIV vaccine to reduce the spread of HIV infections. Developing vaccines for HIV has been challenging. Stopping combination antiretroviral therapy (cART) leads to the re-emergence. Immune privileged areas are able to shield HIV from the immune system. See Churchill et al., Nat Rev Microbiol. 2016, 14:55-60.

HIV-1 has surface spikes made up of trimeric viral envelope glycoprotein (Env) proteins containing a membrane-anchored subunit gp41 and surface subunit gp120. Subunit gp120 undergoes conformational changes upon interaction with CD4. Further binding of gp120 to CCR5 and/or CXCR4 in target cell membranes leads to invasion of HIV into the cells by the fusion of the viral and cellular membranes.

Initial HIV vaccines candidates consisted of gp120 subunits. These vaccines elicited antibody responses in all of vaccinated participants, but it was ineffective in preventing HIV-1 infection. More recently, a clinical trial for HIV vaccination, referred to as RV144, involved using a recombinant canarypox HIV vector (ALVAC-HIV) plus two recombinant gp120 boosts (AIDSVAX B/E). ALVAC-HIV is a live recombinant canarypox vector vaccine that expresses HIV-1 gag, protease, and gp120 linked to the transmembrane anchoring portion of gp41. A post hoc analysis in vaccine efficacy revealed an early peak in vaccine efficacy in the first year, which declined thereafter. See Robb et al. Lancet Infect Dis. 2012, 12:531-537. It is reported that viral evolution was a response to the RV144 HIV vaccination suggesting immune pressure is exerted on the HIV virus. See Gao et al, Viruses, 2018, 10 (4), pii: E167. The generation of an antibody response capable of neutralizing a broad range of clinical isolates remains a major challenge in human immunodeficiency virus type 1 (HIV-1) vaccine development. Thus, there is a need to identify improved therapeutic or preventative strategies.

Sanders et al. report cleaved, soluble HIV-1 Env Trimer, BG505 SOSIP.664 gp140, expresses multiple epitopes for broadly neutralizing but not non-neutralizing antibodies. PLOS Pathog, 2012, 9 (9): e1003618.

Sharma et al. report cleavage-independent HIV-1 env trimers engineered as soluble native spike mimetics for vaccine design. Cell Reports, 2015, 11, 539-550.

Kong et al. report uncleaved prefusion-optimized gp140 trimers derived from analysis of HIV-1 envelope metastability. Nat Commun, 2016, 7:12040-12040. See also US Patent App. Publ. Nos. 2020/0230229 and 2020/0165303.

References cited herein are not an admission of prior art.

SUMMARY

This disclosure relates to modified HIV envelope proteins or envelope protein fragments, or trimeric complexes thereof which have uses in vaccination methods or therapeutic strategies. In certain embodiments, this disclosure relates to modified HIV envelope proteins or envelope protein fragments, or trimeric complexes thereof, comprising an arginine (R) at position 166, glutamine (Q) at position 170, and an amino acid histidine (H) at position 173. In certain embodiments, this disclosure relates to nucleic acids and recombinant vectors encoding said proteins.

In certain embodiments, the modified HIV envelope protein is non-naturally occurring. In certain embodiments, the gp120 domain or fragment thereof is conjugated to the gp41 domain or fragment thereof. In certain embodiments, the envelope protein or envelope protein fragment contains one or more amino acids substituted with cysteine (C) or the envelope protein or envelope protein fragment contains a flexible linker comprising the amino acids glycine or serine, such as a flexible linker comprising polyglycine or poly (glycine-serine) or a polyglycine and serine (e.g. $G_4SG_4S$ SEQ ID NO: 6) between a gp120 domain or fragment thereof and a gp41 domain or fragment thereof.

In certain embodiments, the modified HIV envelope protein is derived from different HIV-1 strains or subtypes.

In certain embodiments the modified HIV envelope protein, fragment, or trimeric complex comprises the amino acid sequence of RDKKQKVH (SEQ ID NO: 2). In certain embodiments, the modified HIV envelope protein comprises or consists of the amino acid sequence of (SEQ ID NO: 3, 1086C UFO-V2HS-RQH)

```
MEGSWVTVYYGVPVWKEAKTTLFCASDAKAYEKKVHNVWATHACVPTDP
NPQEMVLANVTENFNMWKNDMVEQMHEDIISLWDESLKPCVKLTPLCVT
LNCTNVKGNESDTSEVMKNCSFNATTELRDKKQKVHALFYKLDVVPLNG
NSSSSGEYRLINCNTSAITQACPKVSFDPIPLHYCAPAGFAILKCNNKT
FNGTGPCRNVSTVQCTHGIKPVVSTQLLLNGSLAEEEIIIRSENLTNNA
KTIIVHLNESVNIVCTRPNNNTRKSIRIGPGQWFYATGDIIGNIRQAHC
NISESKWNNTLQKVGEELAKHFPSKTIKFEPSSGGDLEITTHSFNCRGE
FFYCNTSDLFNGTYRNGTYNHTGRSSNGTITLQCKIKQIINMWQEVGRP
```

-continued

```
IYAPPIEGEITCNSNITGLLLLRDGGQSNETNDTETFRPGGGDMRDNWR

SELYKYKVVEIKPLGVAPTEAKRRVVEGGGGSGGGGSAVGIGAVFLGFL

GAAGSTMGAASMTLTVQARQLLSGNPDWLPDMTVWGIKQLQARVLAIER

YLKDQQLLGMWGCSGKLICTTAVPWNSSWSNKSQNEIWGNMTWMQWDRE

INNYTNTIYRLLEDSQNQQEKNEKDLLALD,
```

or variant having greater than 70%, 80%, 85%, 90%, 91%, 92%, 93%, 94%, or 95% sequence identity provided that in the variant position 166 is arginine (R), position 170 is glutamine (Q), and position 173 is histidine (H).

In certain embodiments, this disclosure relates to nucleic acids encoding a protein disclosed herein. In certain embodiments, this disclosure relates to vectors comprising a nucleic acid encoding a protein disclosed herein in operable combination with a heterologous promoter. In certain embodiments, this disclosure relates to expression systems comprising a vector comprising a nucleic acid encoding a protein disclosed herein.

In certain embodiments, this disclosure relates to a virus-like particle (VLP) or a self-assembling nanoparticle comprising a protein disclosed herein or trimeric complex thereof on the exterior of the particle.

In certain embodiments, this disclosure relates to vaccines and pharmaceutical compositions comprising a protein, a trimeric protein complex comprising the protein, particle comprising the trimeric protein complex, or a vector encoding the same and a pharmaceutically acceptable excipient.

In certain embodiments, this disclosure relates to methods of vaccinating for HIV comprising administering an effective amount of a protein disclosed herein or fragment thereof, a trimeric protein complex comprising the protein or fragment, a particle comprising the trimeric complex, or a vector encoding the protein, to a subject.

In certain embodiments, this disclosure relates to methods of treating a subject with an HIV infection comprising administering an effective amount of a protein disclosed herein or fragment, a trimeric protein complex comprising the protein or fragment, a particle comprising a trimeric complex, or a vector encoding the protein to a subject in need thereof.

In certain embodiments, this disclosure relates to methods, wherein the protein, fragment, trimeric protein complex, particle, or vector encoding the protein is administered in combination with an adjuvant.

In certain embodiments, this disclosure relates to methods wherein the protein, fragment, trimeric protein complex, particle, or vector encoding the protein is administered in combination with an antiviral agent.

DETAILED DISCUSSION

Figure 1A:
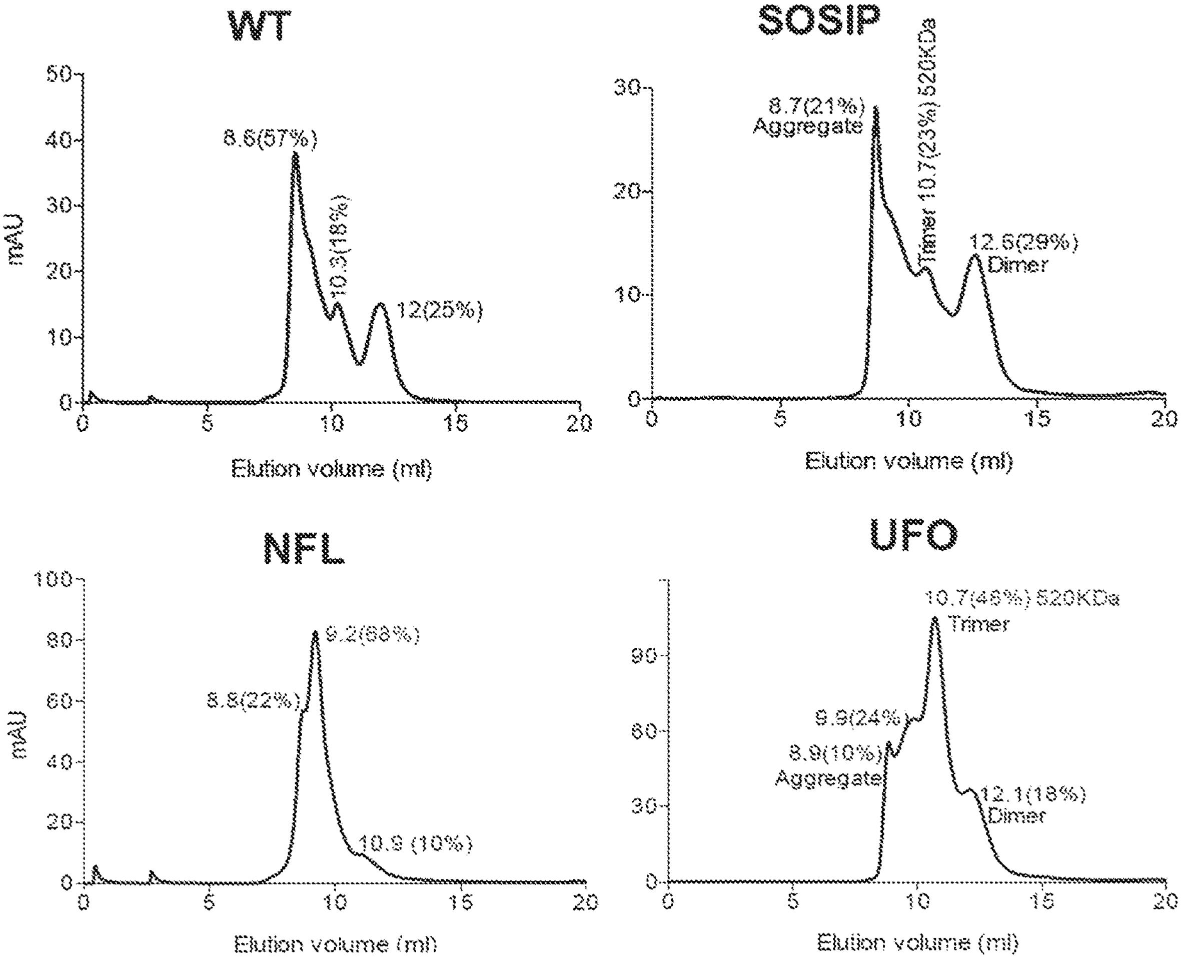
FIG. 1A shows gel filtration profile (elution volume and percent trimeric fraction) of different trimeric variants of 1086C namely, WT, SOSIP, NFL (Native Flexible Linker), and UFO (Uncleaved preFusion Optimized) proteins.
Figure 1B:
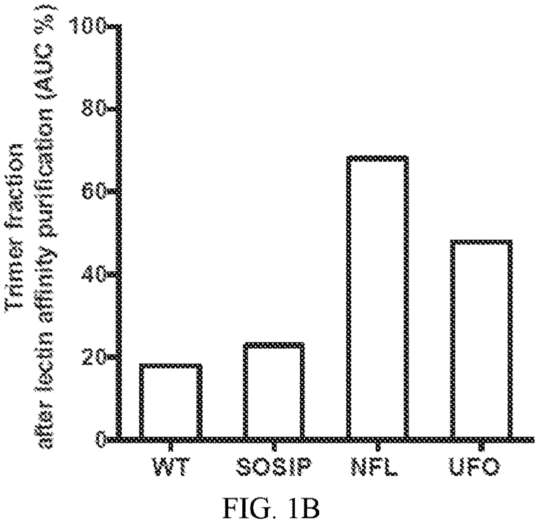
FIG. 1B shows lectin affinity purification of WT, SOSIP, NFL and UFO proteins, and trimeric peak was collected by gel filtration using a Superdex™ 200 Increase 200 10/300 GL increase column. These proteins were expressed by 293F cells, transfected with the plasmid of interest. Supernatant was harvested 4 days after transfection.
Figure 1C:
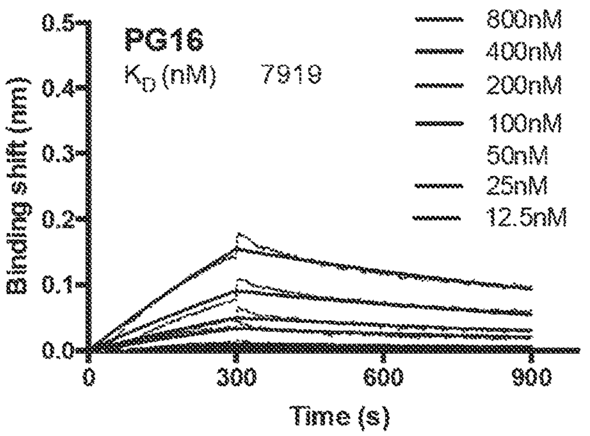
FIG. 1C shows binding of PG16 to NFL variant by Bio Layer Interferometry™ method. OctetRed384 was used for the experiments. Antibodies of interest were captured onto anti human Fc biosensor. Proteins at indicated concentrations were passed as analyte with $K_{on}$=300s and $K_{off}$=600s. Data was fitted to a 1:1 Global Binding Model™.
Figure 1D:
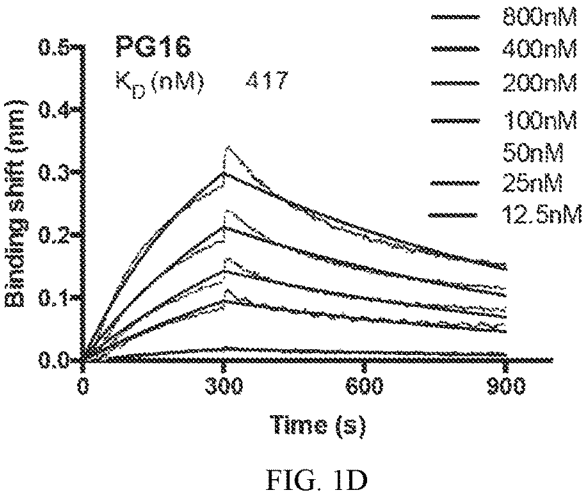
FIG. 1D shows binding of PG16 to UFO variant by Bio Layer Interferometry™ method.
Figure 2:
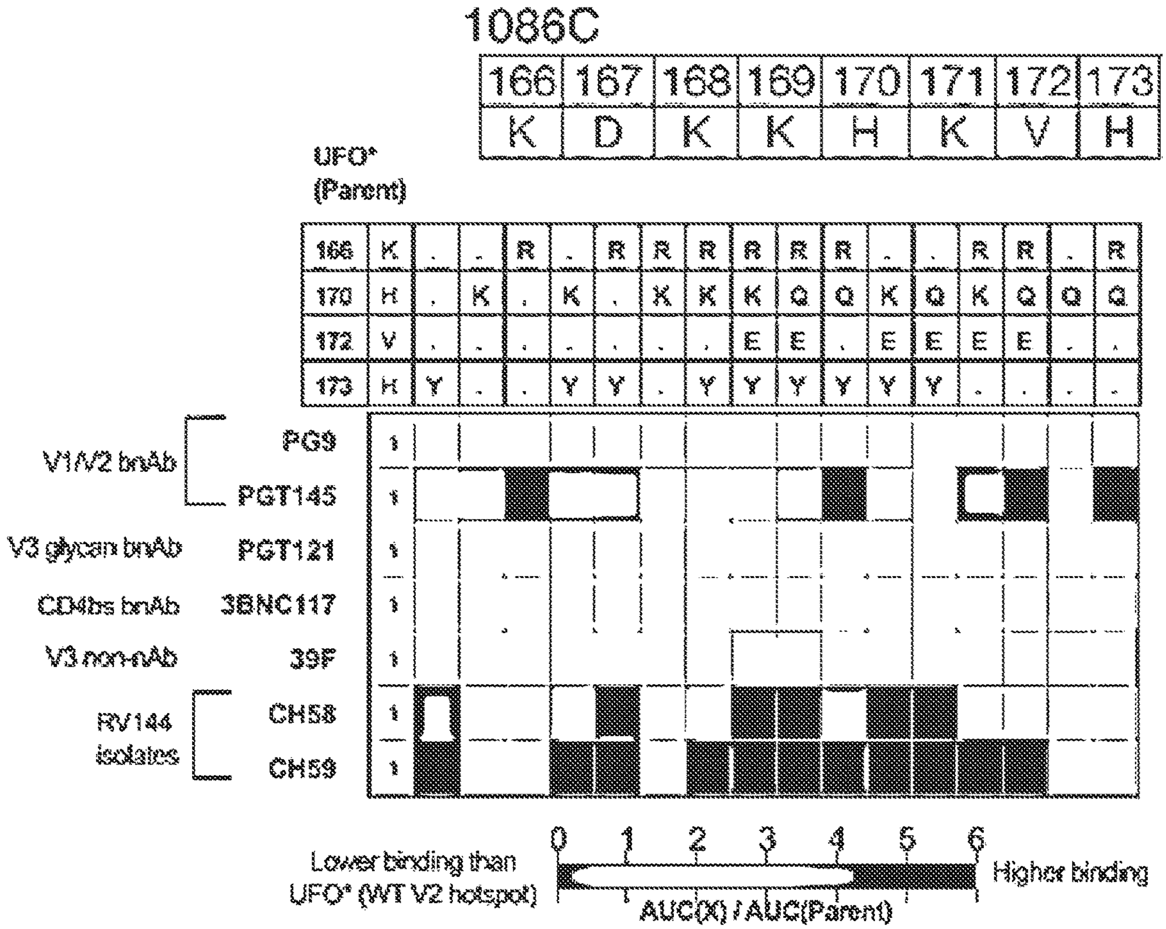
FIG. 2 shows sequence analyses to identify enhance binding of 1086C UFO* or UFO-v2 protein to V1V2 trimer specific broadly neutralizing antibodies (bnAb; e.g. PGT145). 1086C UFO was stabilized, i.e. referred as UFO* or UFO-v2, by introducing A433P, E64K, and A316W. Both UFO and UFO* bound weekly to V1V2 specific bnAb PGT145. V2 hotspot sequence of 1086C and Tier-2 consensus Clade C sequence is also shown. The positions were mutated to either dominant or subdominant amino acids present in consensus. The mutant plasmids were transfected in 293T cells. The culture supernatant harvested after 48h was screened for binding to various bnAbs. All mutants with K166R showed an increase in binding to PGT145, as evident by the BLI data.
Figure 3:
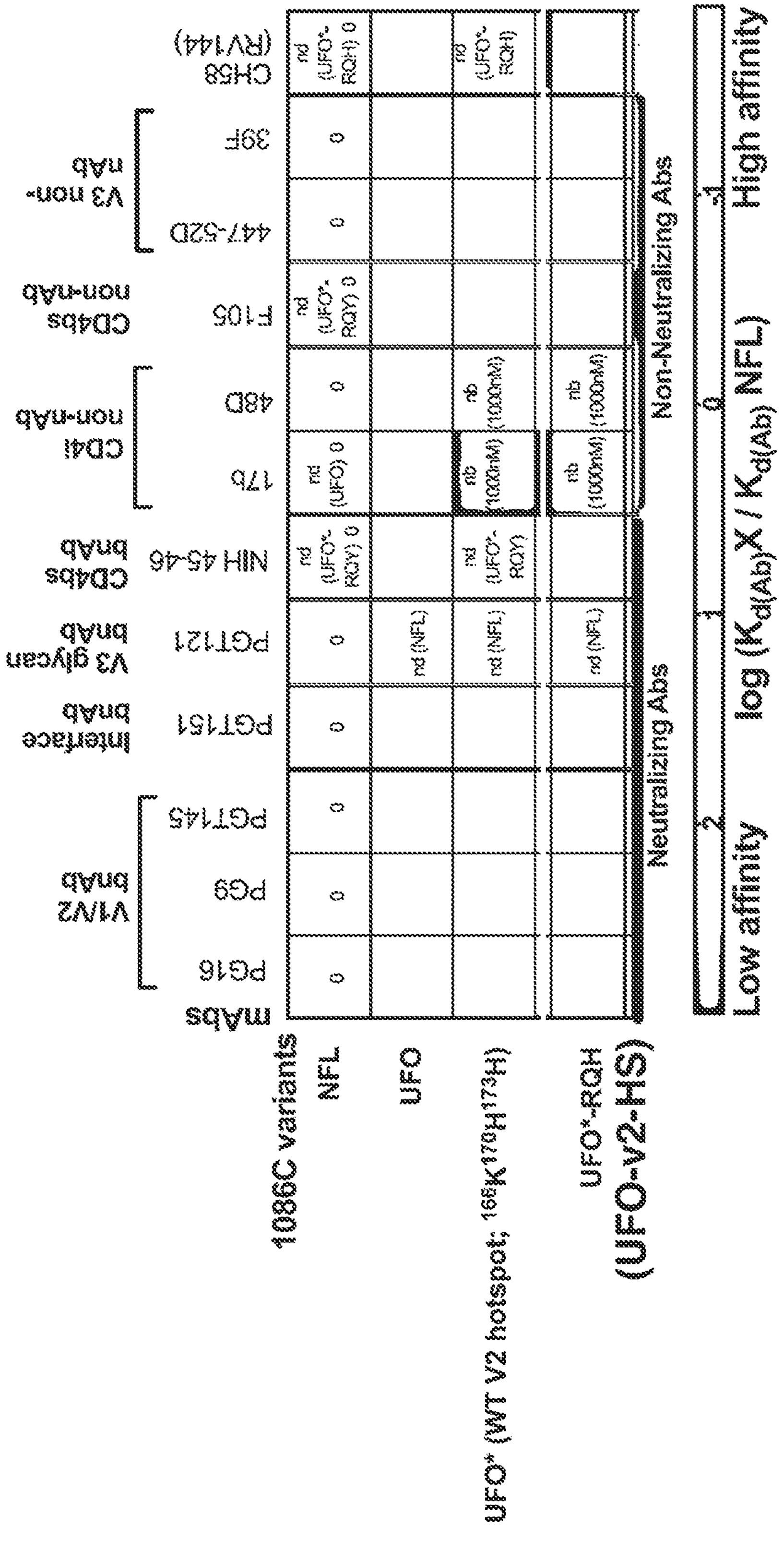
FIG. 3 shows Ab binding profile of NFL, UFO, UFO* and UFO*-RQH by BLI technique. UFO*-RQH also referred as UFO-v2-HS (RQH) showed increase binding to specifically V1V2 directed bnAbs and reduced binding to non-neutralizing antibodies.
Figure 4A:
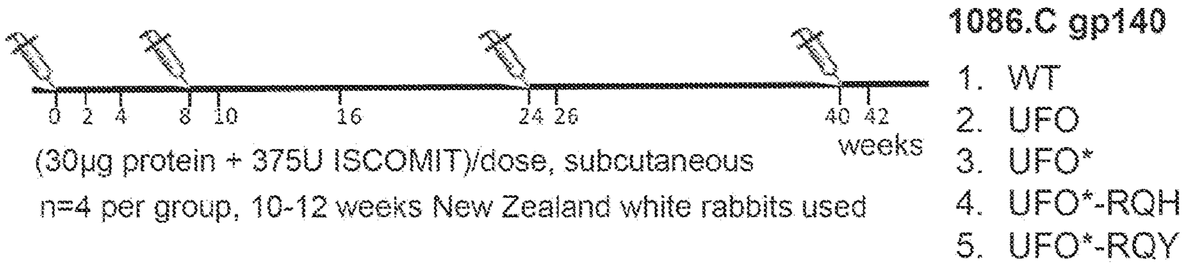
FIG. 4A illustrates experiments in rabbits to monitor the immunogenicity profiles of the 1086C variants in different groups. Five groups with 4 rabbits each were immunized with (1) WT, (2) UFO, (3) UFO* (4) UFO*-RQH (5) UFO*-RQY protein (30 ug protein+375U of ISCOMIT/dose, subcutaneous) at indicated weeks. Serum was collected 2 weeks after each immunization.
Figure 4B:
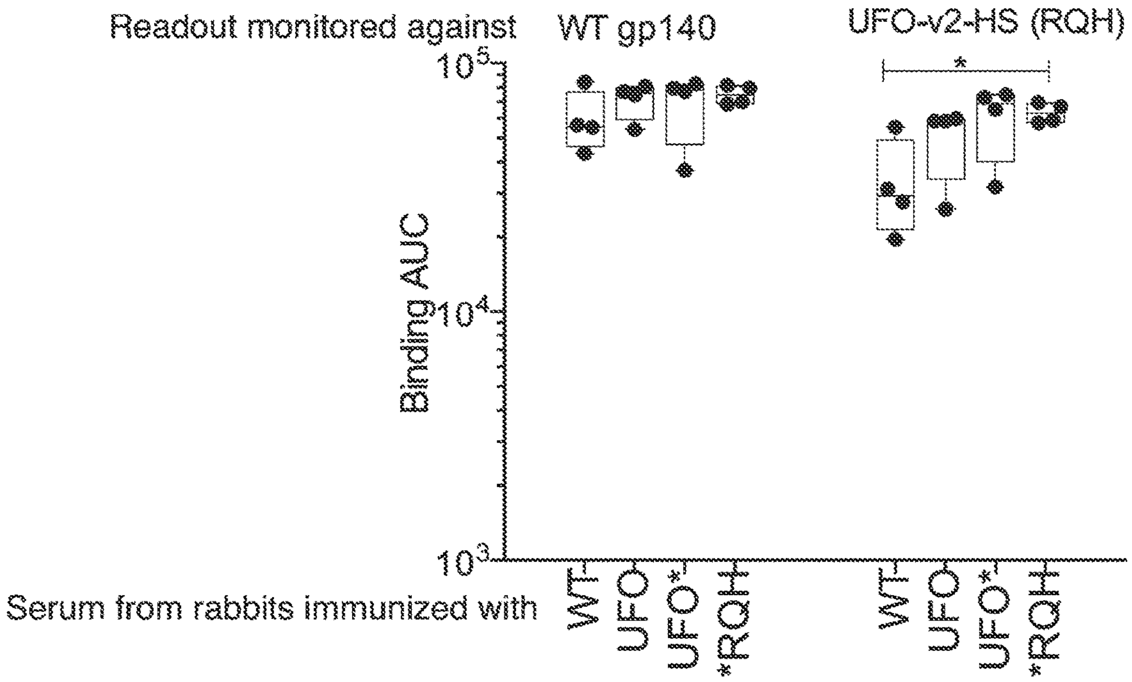
FIG. 4B shows data indicating a significant boost in trimeric 1086C specific antibody response by stabilized UFO-v2-HS (*RQH) immunogen. Binding of serum from immunized group to either WT gp140 or trimeric UFO-v2-HS (RQH) was monitored by Binding Antibody Multiplex Assay™.
Figure 5:
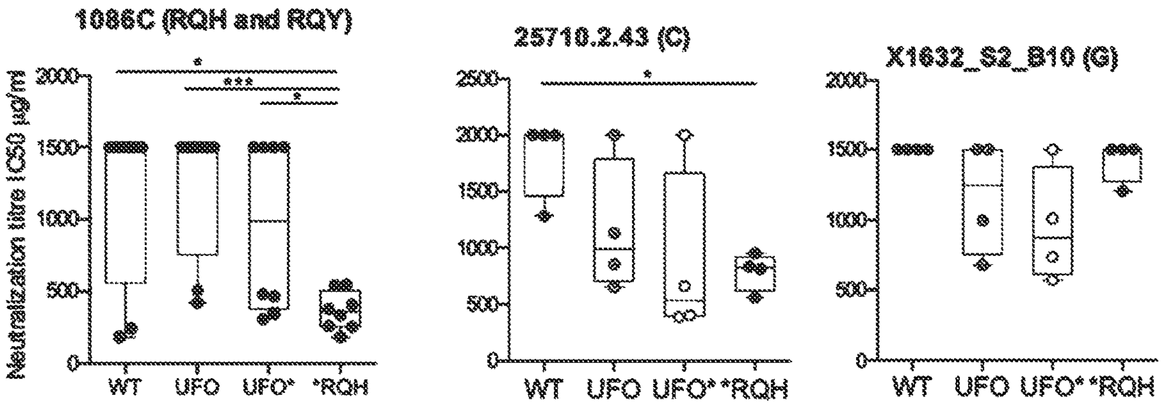
FIG. 5 shows data indicating higher tier-2 neutralization response elicited by UFO-v2-HS (*RQH) and UFO variants. Neutralization assays against the indicated pseudo-viruses were done using TzMbl cells using purified IgGs from immunized rabbit serum.
Figure 6:
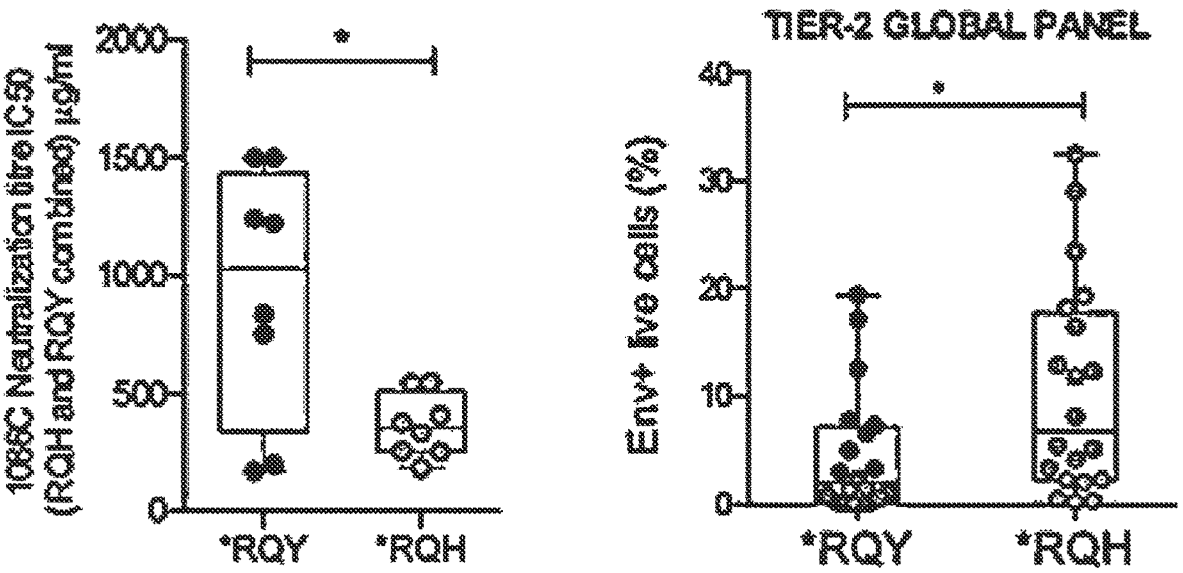
FIG. 6 shows influence of the amino acid in position 173 on immune response elicited (comparison between UFO*RQH and UFO*RQY immunogens). Similar binding antibody titers were induced by either UFO*RQH or UFO*RQY immunogens against WT or trimeric 1086C. Increased homologous neutralization titers and increased binding to membrane anchored envelopes (tier-2) by UFO*RQH variant was observed compared to that of the UFO*RQY variant.

Before the present disclosure is described in greater detail, it is to be understood that this disclosure is not limited to embodiments described, and as such may, of course, vary. It is also to be understood that the terminology used herein is for describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. As such, the terms "a", "an", "one or more" and "at least one" can be used interchangeably.

As used in this disclosure and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") have the meaning ascribed to them in U.S. Patent law in that they are inclusive or open-ended and do not exclude additional, unrecited elements or method steps.

"Consisting essentially of" or "consists of" or the like, when applied to methods and compositions encompassed by the present disclosure refers to compositions like those disclosed herein that exclude certain prior art elements to provide an inventive feature of a claim, but which may contain additional composition components or method steps, etc., that do not materially affect the basic and novel characteristic(s) of the compositions or methods, compared to those of the corresponding compositions or methods disclosed herein.

As used herein, the term "conjugated" refers to linking molecular entities through covalent bonds, or by other specific binding interactions, such as due to hydrogen bonding or other van der Walls forces. The force to break a covalent bond is high, e.g., about 1500 pN for a carbon to carbon bond. The force to break a combination of strong protein interactions is typically a magnitude less, e.g., biotin to streptavidin is about 150 pN. Thus, a skilled artisan would understand that conjugation must be strong enough to bind molecular entities in order to implement the intended results.

"Subject" refers to any animal, preferably a human patient, livestock, rodent, monkey or domestic pet. The term is used herein to encompasses apparently healthy, non-HIV-infected individuals or a patient who is known to be infected with, diagnosed with, a pathogen (e.g., an HIV of any clade).

Unless otherwise noted, the terms "antigen" and "immunogen" are used interchangeably to refer to a substance, typically a protein, which is capable of inducing an immune response in a subject. The terms also refer to proteins that are immunologically active in the sense that once administered to a subject (either directly or by administering to the subject a nucleotide sequence or vector that encodes the protein) is able to evoke an immune response of a humoral and/or cellular type directed against that protein. Thus, in some embodiments, the term "immunogen" can broadly encompass polynucleotides that encode polypeptide or protein antigens described herein. Effective amount of a vaccine or other agent that is sufficient to generate a desired response, such as reduce or eliminate a sign or symptom of a condition or disease, such as AIDS. For instance, this can be the amount necessary to inhibit viral replication or to measurably alter outward symptoms of the viral infection, such as increase of T cell counts in the case of an HIV-1 infection. In general, this amount will be sufficient to measurably inhibit virus (for example, HIV) replication or infectivity. When administered to a subject, a dosage will generally be used that will achieve target tissue concentrations (for example, in lymphocytes) that has been shown to achieve in vitro inhibition of viral replication. In some examples, an "effective amount" is one that treats (including prophylaxis) one or more symptoms and/or underlying causes of any of a disorder or disease, for example to treat HIV. In one example, an effective amount is a therapeutically effective amount. In one example, an effective amount is an amount that prevents one or more signs or symptoms of a particular disease or condition from developing, such as one or more signs or symptoms associated with AIDS.

As used herein, the term "combination with" when used to describe administration with an additional treatment means that the agent may be administered prior to, together with, or after the additional treatment, or a combination thereof.

"Amino acid sequence" refers to a sequence composed of any one of the naturally appearing amino acids, amino acids which be chemically modified, or composed of synthetic amino acids.

The terms "protein" and "peptide" and "polypeptide" refer to compounds comprising amino acids joined via peptide bonds and are used interchangeably.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide.

The term "consisting of" in reference to a peptide having an amino acid sequence refers a peptide having the exact number of amino acids in the sequence and not more or having not more than a rage of amino acids expressly specified in the claim. In certain embodiments, the disclosure contemplates that the "N-terminus of a peptide consist of an amino acid sequence," which refers to the N-terminus of the peptide having the exact number of amino acids in the sequence and not more or having not more than a rage of amino acids specified in the claim however the C-terminus may be connected to additional amino acids, e.g., as part of a larger peptide. Similarly, the disclosure contemplates that the "C-terminus of a peptide consist of an amino acid sequence," which refers to the C-terminus of the peptide having the exact number of amino acids in the sequence and not more or having not more than a rage of amino acids specified in the claim however the N-terminus may be connected to additional amino acids, e.g., as part of a larger peptide.

A "chimeric protein" or "fusion protein" is a molecule in which different portions of the protein are derived from different origins such that the entire molecule is not naturally occurring. A chimeric protein may contain amino acid sequences from the same species of different species as long as they are not arranged together in the same way that they exist in a natural state. Examples of a chimeric protein include sequences disclosed herein that are contain one, two or more amino acids attached to the C-terminal or N-terminal end that are not identical to any naturally occurring protein, such as in the case of adding an amino acid containing an amine side chain group, e.g., lysine, an amino acid containing a carboxylic acid side chain group such as aspartic acid or glutamic acid, a polyhistidine tag, e.g. typically four or more histidine amino acids. Contemplated chimeric proteins include those with self-cleaving peptides such as P2A-GSG. See Wang. Scientific Reports 5, Article number: 16273 (2015).

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide. A label includes the incorporation of a radiolabeled amino acid or the covalent attachment of biotinyl moieties to a polypeptide that can be detected by marked avidin for example, streptavidin, containing a fluorescent marker or enzymatic activity that can be detected by optical or colorimetric methods. Various methods of labeling polypeptides and glycoproteins are known in the art and may be used. Examples of labels for polypeptides include, but are not limited to, the following: radioisotopes or radionucleotides (such as 35S or 1311) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, this disclosure contemplates that proteins disclosed herein may be variants. Variants may include 1 or 2 amino acid substitutions or conservative substitutions. Variants may include 3 or 4 amino acid substitutions or conservative substitutions. Variants may include 5 or 6 or more amino acid substitutions or conservative substitutions. Variants include those with not more than 1% or 2% of the amino acids are substituted. Variants include those with not more than 3% or 4% of the amino acids are substituted. Variants include proteins with greater than 80%, 89%, 90%, 95%, 98%, or 99% identity or similarity. In certain embodiments, variants may be conservative or non-conservative substitutions provided that the conservative or non-conservative substitutions are those that do not reduce an activity or function of the recombinant Env protein, such as the ability to elicit an immune response when administered to a subject.

Variant peptides can be produced by mutating a vector to produce appropriate codon alternatives for polypeptide translation. Variants can be tested in functional assays. Certain variants have less than 10%, and preferably less than 5%, and still more preferably less than 2% changes (whether substitutions, deletions, and so on).

Sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG (SEQ ID NO: 9) and GGGGT (SEQ ID NO: 10) have a sequence identity of 4 out of 5 or 80%. For example, the polypeptides GGGPPP (SEQ ID NO: 11) and GGGAPPP (SEQ ID NO: 12) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic-FYW; hydrophobic-A VIL; Charged positive: R K H; Charged negative-D E; Polar-S TN Q.

This disclosure contemplates "variants" or sequence substitutions or modifications of the sequences disclosed herein, including nucleotide and amino acid sequence substitutions or modifications which do not significantly affect or alter the binding characteristics of the polypeptide containing the amino acid sequence or encoded by the nucleotide sequence. Such sequence substitutions or modifications include nucleotide and amino acid substitutions, additions and deletions. Modifications can be introduced into the sequences disclosed herein by standard techniques known in the art, such as site-directed mutagenesis and PCR-mediated mutagenesis. Conservative amino acid substitutions refer to substitutions in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Percent identity can be determined, for example, by comparing sequence information using the GAP computer program, version 6.0, available from the University of Wisconsin Genetics Computer Group (UWGCG). The GAP program utilizes the alignment method of Needleman and Wunsch (J Mol Biol 1970 48:443), as revised by Smith and Waterman (Adv Appl Math 1981 2:482). Briefly, the GAP program defines identity as the number of aligned symbols (i.e., nucleotides or amino acids) which are identical, divided by the total number of symbols in the shorter of the two sequences. The preferred default parameters for the GAP program include: (1) a unitary comparison matrix (containing a value of 1 for identities and 0 for non-identities) and the weighted comparison matrix of Gribskov and Burgess (Nucl Acids Res 1986 14:6745), as described by Schwartz and Dayhoff (eds., Atlas of Protein Sequence and Structure, National Biomedical Research Foundation, Washington, D.C. 1979, pp. 353-358); (2) a penalty of 3.0 for each gap and an additional 0.10 penalty for each symbol in each gap; and (3) no penalty for end gaps.

A "nucleic acid," or "oligonucleotide," refers to a polymer of nucleotides, which may include both sense and anti-sense strands of RNA, cDNA, genomic DNA, and synthetic forms and mixed polymers of the above. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide can be, for example, ribose sugars (a "ribonucleic acid," or "RNA"), or deoxyribose sugars (a "deoxyribonucleic acid," or "DNA"). A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages. "cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein-coding regions, in the same reading frame.

The term "vector" refers to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, termination, and polyadenylation signals. A non-limiting example of a DNA-based expression vector is pCDNA3.1, which can include includes a mammalian expression enhancer and promoter (such as a CMV promoter). Non-limiting examples of viral vectors include adeno-associated virus (AAV) vectors as well as Poxvirus vector (e.g., Vaccinia, MVA, avian Pox, or Adenovirus).

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are contemplated. For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A heterologous promoter refers to a promoter that originating from a different genetic source than a naturally occurring nucleic acid encoding the same protein.

In certain embodiments, a vector optionally comprises a gene vector element (nucleic acid) such as a selectable marker region, lac operon, a CMV promoter, a hybrid chicken β-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Protein "expression systems" refer to in vivo and in vitro (cell free) systems. Systems for recombinant protein expression typically utilize cells (somatic) transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vector, these extracts and components can synthesize proteins of interest. Cell-free systems typically do not contain proteases and enable labelling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38 (13): e141, both hereby incorporated by reference in their entirety.

A "selectable marker" is a nucleic acid introduced into a vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZ (delta) M15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose: galactose-1-phosphate uridyltransferase I (galT), feedback-insensitive α subunit of anthranilate synthase (OASAID), 2-deoxyglucose (2-DOGR), benzyladenine-N-3-glucuronide, *E. coli* threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

The term "adjuvant" refers to a vehicle used to enhance antigenicity. In some embodiments, an adjuvant can include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages).

In some embodiments, the adjuvant is alum, $AlPO_4$, alhydrogel, Lipid-A, Quil-A or purified Quillaja saponins QA-7, QA-17, QA-18, and QA-21 (see U.S. Pat. No. 5,057,540), QS-21 purified plant extract (also referred to as QA-21), Matrix M™, AS01 (composed of liposomes, monophosphoryl lipid A, and QS-21), MF59™ (oil-in-water emulsion containing squalene (4.3%) in citric acid buffer with stabilizing nonionic surfactants Tween™ 80 (0.5%) and Span 85™ (0.5%)), and liposomes containing saturated phospholipids, cholesterol, and monophosphoryl lipid A adjuvants, liposomes (submicron-sized) comprising polyacrylic acid and lecithin. In certain embodiments, saponins are formulated with squalene nanoparticles comprising sorbitan trioleate and polyoxyethylene sorbitan monooleate. Immunostimulatory oligonucleotides (such as those including a CpG motif) can also be used as adjuvants. Adjuvants include biological molecules (a "biological adjuvant"), such as costimulatory molecules. Exemplary adjuvants include 3M-052, IL-2, RANTES, GM-CSF, TNF-alpha, IFN-gamma, G-CSF, LFA-3, CD72, B7-1, B7-2, OX-40L, 4-1BBL and toll-like receptor (TLR) agonists, TLR-9 agonists.

The terms "virus-like particles" or "VLPs" and the like refer to particles that resemble virus particles but are non-infectious because they do not contain viral genetic material. They can be produced through co-expression of proteins, e.g., envelope proteins and/or structural proteins and/or expression of fusion proteins containing structural domains that self-assemble into the virus-like structure. VLPs are generally composed of one or more viral proteins, such as, but not limited to, those proteins referred to as capsid, coat, shell, surface and/or envelope proteins, or particle-forming polypeptides derived from these proteins. VLPs typically form spontaneously upon recombinant expression of the protein(s) in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) Biophys. J. 60:1445-1456; and Hagensee et al. (1994) J. Virol. 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

Ferritin, encapsulin, sulfur oxygenase reductase, lumazine synthase, and pyruvate dehydrogenase are monomeric proteins that self-assemble into globular protein particle complexes. In some examples, ferritin, encapsulin, sulfur oxygenase reductase, lumazine synthase, or pyruvate dehydrogenase monomers are linked to a modified HIV envelope protein disclosed herein and self-assembled into a protein nanoparticle presenting the disclosed antigens on its surface, which can be administered to a subject to stimulate an immune response to the antigen.

Human Immunodeficiency Virus Type 1 (HIV-1)

The goal of vaccine development for human immunodeficiency virus type-1 (HIV-1) is to induce protective or therapeutic broadly neutralizing antibody (bNAb) responses by vaccination. All bNAbs identified thus far target the envelope glycoprotein (Env) trimer on the surface of HIV-1 virions. The precursor Env protein, gp160, is trafficked from the endoplasmic reticulum (ER) to the Golgi and cleaved by cellular proteases of the furin family into its mature form. The cleaved Env trimer engages host receptors to mediate viral entry and is the primary target of humoral immune responses. Functional Env is a trimer of heterodimers, each containing a receptor-binding protein, gp120, and a transmembrane protein, gp41, which are held together by non-covalent interactions. This mature form of Env is metastable as it is poised to undergo dramatic and irreversible conformational changes upon binding to host receptor and co-receptor to mediate membrane fusion. Env metastability also facilitates immune evasion by causing gp120 shedding and generating a diverse assortment of native, more open and non-native conformations.

Various strategies have been proposed in attempts to overcome Env metastability, and to create stable, homogeneous gp140 trimers for structural and vaccine studies. For example, development of the BG505 SOSIP.664 gp140 trimer (Sanders et al., PLOS Pathog. 9 (9): e1003618, 2013) has facilitated high-resolution structural analyses, provided a rational basis for trimer-based vaccine design, allowed expansion of the SOSIP design to other HIV-1 strains and incorporation of new stabilizing mutations, and removal of furin dependency by cleavage site modification. However, a premium is placed on trimer purification in order to minimize unwanted Env forms and misfolded trimers. Complex methods such as broadly HIV-1 neutralizing antibodies affinity purification, negative selection, and multi-cycle SEC have been developed for trimer purification.

HIV-1 can be divided into several different clades, for example A, B, C, D, E, F, G, H, J and K, which vary in prevalence throughout the world. Each clade comprises different strains of HIV-1 which have been grouped together on the basis of their genetic similarity.

The initial phase of the HIV-1 replicative cycle involves the attachment of the virus to susceptible host cells followed by fusion of viral and cellular membranes. These events are mediated by the exterior viral envelope glycoproteins which are first synthesized as a fusion-incompetent precursor envelope glycoprotein (Env) known as gp160. During infection, proteases of the host cell cleave gp160 into gp120 and gp41. Gp41 is an integral membrane protein, while gp120 protrudes from the mature virus. Together gp120 and gp41 make up the HIV-1 Env spike, which is a target for neutralizing antibodies.

Subunit gp120 undergoes conformational changes upon interaction with CD4. Further binding of gp120 to CCR5 and/or CXCR4 in target cell membranes leads to invasion of HIV into the cells by the fusion of the viral and cellular membranes. HIV-1 is reported to be stabilized by interactions between V1-V3 loops at the apex of the trimer spikes. See Julien et al. Science, 2013, 342 (6165): 1477-83.

Most viral vaccines induce neutralizing antibodies, which bind to and inhibit viral entry to target cells. Several initial HIV vaccines candidates, consisted of envelop gp120 subunits, elicited antibody responses but failed in preventing HIV-1 infection. The recent RV144 efficacy trial, the first study to show significant protection in humans, determined a major correlate of protection to be non-neutralizing antibodies directed towards the variable loops 1-2 (V1V2) on the HIV-1 gp120 envelope protein. This correlate has been similarly found in non-human primate vaccine trials. See Robb et al. Lancet Infect Dis. 2012, 12:531-537. In addition to this, the antibodies directed toward a "hotspot" region within the V2 loop have been shown to correlate with decreased risk of infection, suggesting that the V2 loop should be preferentially targeted over the V1 loop for a vaccine response. Because of these findings there is now great interest in the development of vaccine immunogens that can promote substantial V1V2-directed antibody responses.

About 50% of global HIV-1 infections are due to clade C viruses and there is a great need for the development of stabilized natively-like trimeric clade C gp140 protein immunogen for inducing neutralizing antibodies by vaccination. The C.1086 based gp140 trimer would be of interest because unstable C.1086 gp140 protein does not induce autologous neutralizing antibodies.

The HIV-1 Env protein is initially synthesized as a precursor protein of 845-870 amino acids in size. Individual precursor polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp 120-gp41 protomers within the homotrimer. The ectodomain (that is, the extracellular portion) of the HIV-1 Env trimer undergoes several structural rearrangements from a prefusion mature (cleaved) closed conformation that evades antibody recognition, through intermediate conformations that bind to receptors CD4 and co-receptor (either CCR5 or CXCR4), to a post-fusion conformation. The HIV-1 Env ectodomain comprises the gp120 protein (approximately HIV-1 Env positions 31-511) and the gp41 ectodomain (approximately HIV-1 Env positions 512-644). An HIV-1 Env ectodomain trimer comprises a protein complex of three HIV-1 Env ectodomains. As used herein "HIV-1 Env ectodomain trimer" includes both soluble trimers (that is, trimers without gp41 transmembrane domain or cytoplasmic tail) and membrane anchored trimers (for example, trimers including a full-length gp41).

Mature gp120 includes approximately HIV-1 Env residues 31-511, contains most of the external, surface-exposed, domains of the HIV-1 Env trimer, and it is gp120 which binds both to cellular CD4 receptors and to cellular chemokine receptors (such as CCR5). A mature gp120 polypeptide is an extracellular polypeptide that interacts with the gp41 ectodomain to form an HIV-1 Env protomer that trimerizes to form the HIV-1 Env ectodomain trimer. The mature gp120 wild-type polypeptide is heavily N-glycosylated, giving rise to an apparent molecular weight of 120 kD. Native gp120 includes five conserved regions (C1-C5) and five regions of high variability (V1-V5).

Mature gp41 includes approximately HIV-1 Env residues 512-860, and includes a cytosolic-domain, transmembrane-domain, and ecto-domain. The gp41 ectodomain (including approximately HIV-1 Env residues 512-644) can interact with gp120 to form an HIV-1 Env protomer that trimerizes to form the HIV-1 Env trimer.

The prefusion mature closed conformation of the HIV-1 Env ectodomain trimer is a structural conformation adopted by HIV-1 Env ectodomain trimer after cellular processing to a mature prefusion state with distinct gp120 and gp41 polypeptide chains, and before specific binding to the CD4 receptor. The three-dimensional structure of an exemplary HIV-1 Env ectodomain trimer in the prefusion mature closed conformation is known (see, e.g., Pancera et al., Nature, 514:455-461, 2014).

Unless context indicates otherwise, the numbering used in the disclosed HIV-1 Env proteins and fragments thereof (such as a gp120 and gp41) is relative to the HXB2 numbering scheme as set forth in Numbering Positions in HIV Relative to HXB2CG Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, N. Mex., which is incorporated by reference herein in its entirety. For reference, the amino acid sequence of HIV-1 Env of HXB2 is set forth as SEQ ID NO: 1 (envelope polyprotein [Human immunodeficiency virus 1] GenBank: AAB50262.1, incorporated by reference herein as present in the database on October 27,2020).

HXB2 (Clade B, SEQ ID NO: 1):
MRVKEKYQHLWRWGWRWGTMLLGMLMICSATEKLWVTVYYGVPVWKEAT

TTLFCASDAKAYDTEVHNVWATHACVPTDPNPQEVVLVNVTENFNMWKN

DMVEQMHEDIISLWDQSLKPCVKLTPLCVSLKCTDLKNDTNTNSSSGRM

-continued

```
IMEKGEIKNCSFNISTSIRGKVQKEYAFFYKLDIIPIDNDTTSYKLTSC
NTSVITQACPKVSFEPIPIHYCAPAGFAILKCNNKTFNGTGPCTNVSTV
QCTHGIRPVVSTQLLLNGSLAEEEVVIRSVNFTDNAKTIIVQLNTSVEI
NCTRPNNNTRKRIRIQRGPGRAFVTIGKIGNMRQAHCNISRAKWNNTLK
QIASKLREQFGNNKTIIFKQSSGGDPEIVTHSFNCGGEFFYCNSTQLFN
STWFNSTWSTEGSNNTEGSDTITLPCRIKQIINMWQKVGKAMYAPPISG
QIRCSSNITGLLLTRDGGNSNNESEIFRPGGGDMRDNWRSELYKYKVVK
IEPLGVAPTKAKRRVVQREKRAVGIGALFLGFLGAAGSTMGAASMTLTV
QARQLLSGIVQQQNNLLRAIEAQQHLLQLTVWGIKQLQARILAVERYLK
DQQLLGIWGCSGKLICTTAVPWNASWSNKSLEQIWNHTTWMEWDREINN
YTSLIHSLIEESQNQQEKNEQELLELDKWASLWNWFNITNWLWYIKLFI
MIVGGLVGLRIVFAVLSIVNRVRQGYSPLSFQTHLPTPRGPDRPEGIEE
EGGERDRDRSIRLNGSLALIWDDLRSLCLFSYHRLRDLLLIVTRIVELL
GRRGWEALKYWWNLLQYWSQELKNSAVSLLNATAIAVAEGTDRVIEVVQ
GACRAIRHIPRRIRQGLERILL,
```

wherein bold R is position 166, bold Q is position 170, an bold Y is position 173.

The terms "HIV-1 Env ectodomain trimer stabilized in a prefusion mature closed conformation" refer to an HIV-1 Env ectodomain trimer having one or more amino acid substitutions, deletions, or insertions compared to a native HIV-1 Env sequence that provide for increased retention of the prefusion mature closed conformation upon CD4 binding compared to a corresponding native HIV-1 Env sequence. In some embodiments, the HIV-1 Env ectodomain trimer can include one or more cysteine substitutions that allow formation of a non-natural disulfide bond that stabilizes the HIV-1 Env ectodomain trimer in its prefusion mature closed conformation or domains (e.g., gp120 and the gp41) may be linked together by flexible linkers, e.g., linkers that contain mixtures of amino acids glycine, serine, and alanine.

In certain embodiments, a HIV-1 Env ectodomain trimer stabilized in the prefusion mature closed conformation has at least 90% (such as at least 95% or at least 99%) reduced transition to the CD4-bound open conformation upon CD4 binding compared to a corresponding native HIV-1 Env sequence. The "stabilization" of the prefusion mature closed conformation by the one or more amino acid substitutions, deletions, or insertions can be, for example, energetic stabilization (for example, reducing the energy of the prefusion mature closed conformation relative to the CD4-bound open conformation) and/or kinetic stabilization (for example, reducing the rate of transition from the prefusion mature closed conformation to the prefusion mature closed conformation). Additionally, stabilization of the HIV-1 Env ectodomain trimer in the prefusion mature closed conformation can include an increase in resistance to denaturation compared to a corresponding native HIV-1 Env sequence.

Methods of determining if a HIV-1 Env ectodomain trimer is in the prefusion mature closed conformation are provided herein and include (but are not limited to) negative stain electron microscopy and antibody binding assays using a prefusion mature closed conformation specific antibody, such as VRC26 or PGT145. Methods of determining if a HIV-1 Env ectodomain trimer is in the CD4-bound open conformation are also provided herein, and include (but are not limited to) negative stain electron microscopy and antibody binding assays using a CD4-bound open conformation specific antibody, such as 17b, which binds to a CD4-induced epitope. Transition from the prefusion mature closed conformation upon CD4 binding can be assayed, for example, by incubating a HIV-1 Env ectodomain trimer of interest that is in the prefusion mature closed conformation with a molar excess of CD4, and determining if the HIV-1 Env ectodomain trimer retains the prefusion mature closed conformation (or transitions to the CD4-bound open conformation) by negative stain electron microscopy analysis, or antigenic analysis.

The term "HIV-1 gp140" refers to a recombinant HIV Env polypeptide including gp120 and the gp41 ectodomain, but not the gp41 transmembrane or cytosolic domains. HIV-1 gp140 polypeptides can trimerize to form a soluble HIV-1 Env ectodomain trimer.

The term "HIV-1 gp145" refers to a recombinant HIV Env polypeptide including gp120, the gp41 ectodomain, and the gp41 transmembrane domain. HIV-1 gp145 polypeptides can trimerize to form a membrane-anchored HIV-1 Env ectodomain trimers.

The term "HIV-1 gp160" refers to a recombinant HIV Env polypeptide including gp120 and the entire gp41 protein (ectodomain, transmembrane domain, and cytosolic tail).

An "HIV-1 neutralizing antibody" refers to an antibody that reduces the infectious titer of HIV-1 by binding to HIV-1 Env protein and inhibiting HIV-1 function. In some embodiments, neutralizing antibodies to HIV-1 can inhibit the infectivity of multiple strains of HIV-1. In some embodiments, a disclosed immunogen can be administered to a subject to elicit an immune response that includes production of antibodies that specifically bind to the HIV-1 Env fusion peptide and neutralize strains of HIV-1 from HIV-1 clade C or multiple HIV-1 clades.

In one example, a desired response is to induce an immune response that inhibits or prevents HIV-1 infection. The HIV-1 infected cells do not need to be completely eliminated or prevented for the composition to be effective. For example, administration of an effective amount of the immunogen can induce an immune response that decreases the number of HIV-1 infected cells (or prevents the infection of cells) by a desired amount, for example, by at least 50%, at least 60%, at least 70%, at least 80%, at least 90%, at least 95%, at least 98%, or even at least 100% (elimination or prevention of detectable HIV-1 infected cells), as compared to the number of HIV-1 infected cells in the absence of the immunization.

Modified HIV Envelope Proteins or Envelope Protein Fragments, or Trimeric Complexes Thereof In certain embodiments, this disclosure relates to modified HIV envelope proteins or envelope protein fragments, or trimeric complexes thereof, comprising an arginine (R) at position 166, glutamine (Q) at position 170, and an amino acid histidine (H) at position 173.

In certain embodiments the protein comprises the amino acid sequence of RDKKQKVH (SEQ ID NO: 2). In certain embodiments, the HIV envelope protein comprises or consists of the amino acid sequence of

```
                    (SEQ ID NO: 3, 1086C UFO-V2HS-RQH)
MEGSWVTVYYGVPVWKEAKTTLFCASDAKAYEKKVHNVWATHACVPTDP
NPQEMVLANVTENFNMWKNDMVEQMHEDIISLWDESLKPCVKLTPLCVT
```

-continued
LNCTNVKGNESDTSEVMKNCSFNATTELRDKKQKVHALFYKLDVVPLNG

NSSSSGEYRLINCNTSAITQACPKVSFDPIPLHYCAPAGFAILKCNNKT

FNGTGPCRNVSTVQCTHGIKPVVSTQLLLNGSLAEEEIIIRSENLTNNA

KTIIVHLNESVNIVCTRPNNNTRKSIRIGPGQWFYATGDIIGNIRQAHC

NISESKWNNTLQKVGEELAKHFPSKTIKFEPSSGGDLEITTHSFNCRGE

FFYCNTSDLFNGTYRNGTYNHTGRSSNGTITLQCKIKQIINMWQEVGRP

IYAPPIEGEITCNSNITGLLLLRDGGQSNETNDTETFRPGGGDMRDNWR

SELYKYKVVEIKPLGVAPTEAKRRVVEGGGGSGGGGSAVGIGAVFLGFL

GAAGSTMGAASMTLTVQARQLLSGNPDWLPDMTVWGIKQLQARVLAIER

YLKDQQLLGMWGCSGKLICTTAVPWNSSWSNKSQNEIWGNMTWMQWDRE

INNYTNTIYRLLEDSQNQQEKNEKDLLALD, or variant having greater than 70%, 80%, 85%, 90%, 91%, 92%, 93%, 94%, or 95% sequence identity provided that position 166 is arginine (R), position 170 is glutamine (Q), and position 173 is histidine (H).

In certain embodiments, this disclosure relates to modified HIV envelope proteins or envelope protein fragments, or trimeric complexes thereof, comprising an arginine (R) at position 166, glutamine (Q) at position 170, and an amino acid tyrosine (Y) at position 173.

In certain embodiments the modified HIV envelope protein comprises the amino acid sequence of RDKKQKVY (SEQ ID NO: 4). In certain embodiments, the modified HIV envelope protein comprises the amino acid sequence of (SEQ ID NO: 5, 1086C UFO-V2HS-RQY)
MEGSWVTVYYGVPVWKEAKTTLFCASDAKAYEKKVHNVWATHACVPTDP

NPQEMVLANVTENFNMWKNDMVEQMHEDIISLWDESLKPCVKLTPLCVT

LNCTNVKGNESDTSEVMKNCSFNATTELRDKKQKVYALFYKLDVVPLNG

NSSSSGEYRLINCNTSAITQACPKVSFDPIPLHYCAPAGFAILKCNNKT

FNGTGPCRNVSTVQCTHGIKPVVSTQLLLNGSLAEEEIIIRSENLTNNA

KTIIVHLNESVNIVCTRPNNNTRKSIRIGPGQWFYATGDIIGNIRQAHC

NISESKWNNTLQKVGEELAKHFPSKTIKFEPSSGGDLEITTHSFNCRGE

FFYCNTSDLFNGTYRNGTYNHTGRSSNGTITLQCKIKQIINMWQEVGRP

IYAPPIEGEITCNSNITGLLLLRDGGQSNETNDTETFRPGGGDMRDNWR

SELYKYKVVEIKPLGVAPTEAKRRVVEGGGGSGGGGSAVGIGAVFLGFL

GAAGSTMGAASMTLTVQARQLLSGNPDWLPDMTVWGIKQLQARVLAIER

YLKDQQLLGMWGCSGKLICTTAVPWNSSWSNKSQNEIWGNMTWMQWDRE

INNYTNTIYRLLEDSQNQQEKNEKDLLALD, or variant having greater than 70%, 80%, 85%, 90%, 91%, 92%, 93%, 94%, or 95% sequence identity provided that position 166 is arginine (R), position 170 is glutamine (Q), and position 173 is tyrosine (Y).

In certain embodiments, the modified HIV envelope protein or trimer specifically binds to an antibody with a dissociation constant of less than $10^{-6}$ Molar, such as less than $10^{-7}$ Molar, less than $10^{-8}$ Molar, or less than $10^{-9}$ Molar. In some embodiments, the modified HIV envelope protein specifically bound by an antibody that specifically binds to the V1V2 domain on a trimer, but not a monomer. Exemplary antibodies with such antigen binding characteristics include the PGT141, PGT142, PGT143, PGT144, PGT145, and VRC26 antibodies. Additional examples include the PG9, PG16, and CH01-CH04 antibodies. Accordingly, in some embodiments the modified HIV envelope protein or trimer specifically binds to an antibody (such as a PGT141, PGT142, PGT143, PGT144, PGT145, and VRC26 antibody) that specifically binds to the VIV2 domain in its trimeric, but not monomeric, form with a dissociation constant of less than $10^{-6}$ Molar, such as less than $10^{-7}$ Molar, less than $10^{-8}$ Molar, or less than $10^{-9}$ Molar. The determination of specific binding may readily be made by using or adapting routine procedures, such as ELISA, immune competition, surface plasmon resonance, or other immunosorbent assays.

In some embodiments, the modified HIV envelope protein includes an N-linked glycosylation site at position 332 (if not already present on the ectodomain). For example, by T332N substitution in the case of BG505-based immunogens. The presence of the glycosylation site at N332 allows for binding by 2G12 antibody.

In some embodiments, the modified HIV envelope protein includes a lysine residue at HIV-1 Env position 168 (if not already present on the ectodomain). For example, the lysine residue can be added by amino acid substitution (such as an E168K substitution in the case of the JR-FL based immunogens). The presence of the lysine residue at position 168 allows for binding of particular broadly neutralizing antibodies to the V1V2 loop of gp120.

In certain embodiments, the modified HIV envelope protein is non-naturally occurring, e.g., because the envelope protein or envelope protein fragment contains one or more amino acids substituted with cysteine (C) or because the envelope protein or envelope protein fragment contains a flexible linker comprising the amino acids glycine, serine, or alanine, such as a flexible linker comprising polyglycine or poly(glycine-serine) or a polyglycine and serine (e.g. $G4SG_4S$ SEQ ID NO: 6) between a gp120 domain or fragment thereof and a gp41 domain or fragment thereof.

In certain embodiments, the modified HIV envelope protein is non-naturally occurring because HIV-1 envelope protein comprises an engineered disulfide bond between gp 120 and gp41. In certain embodiments, the engineered disulfide bond is between residues A501C and T605C. In certain embodiments, the modified HIV envelope protein comprises the stabilizing mutation I559P.

In certain embodiments, the modified HIV envelope protein is non-naturally occurring because of a non-natural disulfide bond between HIV-1 Env positions 201 and 433 (e.g., by introduction of I201C and A433C substitutions).

In some embodiments, the modified HIV-1 envelope protein is non-naturally occurring because the envelope protein contains (a) a linker sequence, e.g., (G4S) 2 (SEQ ID NO: 6) that substitutes for residues 508-511 at the cleavage site, and (b) an engineered disulfide bond between residues A501C and T605C.

In certain embodiments, the modified HIV envelope protein is non-naturally occurring because the envelope protein comprising a gp 120 polypeptide and a gp41 polypeptide or fragment, wherein amino acid residues 548-568 of the N-terminus of heptad 1 region (HR1) of the gp41 polypeptide is replaced with a linker (loop) sequence of 6 to 14 amino acid residues in length. In certain embodiments the loop sequence is a poly(glycine-serine).

In certain embodiments, the modified HIV envelope protein is derived from different HIV-1 strains or subtypes.

In some embodiments, a modified HIV envelope protein may a include modified glycan site at residue 332 (T332N).

In some other embodiments, the modified HIV envelope protein harbors mutations or alterations introduced at the cleavage site, e.g., replacing REKR (SEQ ID NO: 7) with RRRRRR (SEQ ID NO: 8). In various embodiments, the C terminus of the modified HIV envelope protein can be truncated to either residue 664 or 681 (according to HXB2 nomenclature), resulting in the gp140 versions like "BG505 SOSIP.gp140.664" and "BG505 SOSIP.gp140.681" which are known in the art. Also, the HIV-1 immunogens of this disclosure can employ the different gp 140 derived proteins from various HIV-1 clades or strains (e.g., strains BG505 (clade A), JRFL (clade B) CAP45 (clade C), ZM109 (clade C), DU172.17 (clade C), and CH115.12 (clade B'/C)).

In certain embodiments, a modified HIV envelope protein is non-naturally occurring because HIV-1 envelope protein comprises an engineered disulfide bond between gp 120 and gp41. In certain embodiments, the engineered disulfide bond is between residues A501C and T605C. In some of these embodiments, the engineered disulfide bond is between residues A501C and T605C and comprises the stabilizing mutation I559P.

In some embodiments, a modified HIV-1 envelope protein is non-naturally occurring because the envelope protein contains a linker sequence (G4S) 2 (SEQ ID NO: 6) that substitutes for residues 508-511 at the cleavage site.

In certain embodiments, a modified HIV envelope protein is non-naturally occurring because the envelope protein comprising a gp 120 polypeptide and a gp41 polypeptide or fragment, wherein amino acid residues 548-568 of the N-terminus of heptad 1 region (HR1) of the gp41 polypeptide is replaced with a linker (loop) sequence of 6 to 14 amino acid residues in length. In certain embodiments the loop sequence is a poly(glycine-serine).

In certain embodiments, a modified HIV envelope protein comprises one or more amino acid substitutions to remove N-linked glycosylation sites at one or more of HIV-1 Env positions N88, N230, N241, and N611.

In certain embodiments, the modified HIV envelope protein is derived from different HIV-1 strains or subtypes.

In certain embodiments, the modified HIV envelope protein typically does not include a signal peptide (for example, the recombinant gp120 protein typically does not include HIV-1 Env positions 1-30), as the signal peptide is proteolytically cleaved during cellular processing. Additionally, in several embodiments, the gp41 ectodomain includes the extracellular portion of gp41 (e.g., positions 512-664). In certain embodiments, the modified HIV envelope protein the gp41 ectodomain is not linked to a transmembrane domain or other membrane anchor. In certain embodiments, the modified HIV envelope protein the C-terminus of the gp41 ectodomain is linked to a transmembrane domain. In certain embodiments, the modified HIV envelope protein has N-terminal residue of the gp120 protein positions 1-35. In certain embodiments, the modified HIV envelope protein has C-terminal residue of the gp120 protein positions 503-511. In certain embodiments, the modified HIV envelope protein has N-terminal residue of the gp41 ectodomain positions 512-522. In certain embodiments, the modified HIV envelope protein the C-terminal residue of the gp41 ectodomain is one of HIV-1 Env positions 624-705.

In certain embodiments, it is contemplated that modified HIV envelope proteins, fragments, and trimeric complexes comprising the same as disclosed herein are presented on nanoparticles and virus like particle, e.g., constructs that are expressed wherein the C-terminus of an HIV envelope protein is fused to the N-terminus of ferritin subunit to form nanoparticles.

In certain embodiments, it is contemplated that modified HIV envelope proteins trimer can include modifications, such as amino acid substitutions, deletions or insertions, glycosylation and/or covalent linkage to unrelated proteins (e.g., a protein tag), as long as the modified HIV envelope proteins can form the trimer.

In certain embodiments, it is contemplated that modified HIV envelope proteins can be linked to an exogenous multimerization (trimerization) domains.

In certain embodiments, it is contemplated that the modified HIV envelope protein or trimers are soluble in aqueous solution. In some embodiments, the trimer dissolves to a concentration of at least 0.5 mg/ml (such as at least 1.0 mg/ml, 1.5 mg/ml, 2.0 mg/ml, 3.0 mg/ml, 4.0 mg/ml or at least 5.0 mg/ml) in phosphate buffered saline (pH 7.4) at room temperature (e.g., 20-22 degrees Celsius) and remains dissolved for at least for at least 12 hours (such as at least 24 hours, at least 48 hours, at least one week, at least two weeks, or more time). In one embodiment, the phosphate buffered saline includes NaCl (137 mM), KCl (2.7 mM), $Na_2HPO_4$ (10 mM), $KH_2PO_4$ (1.8 mM) at pH 7.4. In some embodiments, the phosphate buffered saline further includes $CaCl_2$) (1 mM) and $MgCl_2$ (0.5 mM).

Methods of Use

In certain embodiments, this disclosure relates to methods of vaccinating for HIV comprising administering an effective amount of a protein disclosed herein, a trimeric protein complex comprising the protein, a particle comprising the trimeric protein, or a vector encoding the protein to a subject.

In certain embodiments, this disclosure relates to methods of treating a subject with an HIV infection comprising administering an effective amount of a protein disclosed herein, a trimeric protein complex comprising the protein, a particle comprising the trimeric protein, or a vector encoding the protein to a subject in need thereof.

In certain embodiments, this disclosure relates to methods, wherein the protein, trimeric protein complex, particle, or vector encoding the protein is administered in combination with an adjuvant.

In certain embodiments, this disclosure relates to methods wherein the protein, trimeric protein complex, particle, or vector encoding the protein is administered in combination with an antiviral agent.

In certain embodiments, this disclosure relates to methods of vaccinating or immunizing for HIV comprising administering to the subject a priming composition followed by a boosting composition.

In certain embodiments, this disclosure relates to methods of vaccinating or immunizing comprising: i) administering to a human subject a nucleic acid and/or recombinant virus that encodes an Env protein of HIV or segment thereof as reported herein under conditions such that virus-like particles with surface Env spike proteins are formed in the subject; and ii) administering to the human subject an effective amount of HIV envelope proteins or envelope protein fragments, or trimeric complexes thereof or a nucleic acid encoding HIV envelope proteins or envelope protein fragments, or trimeric complexes thereof reported herein.

In certain embodiments, the methods are conducted in combination with an adjuvant. When inhibiting, treating, or preventing HIV-1 infection, the methods can be used either to avoid infection in an HIV-1 seronegative subject (e.g., by inducing an immune response that protects against HIV-1 infection), or to treat existing infection in an HIV-1 seropositive subject. The HIV-1 seropositive subject may or may not carry a diagnosis of AIDS. Hence in some embodiments the methods involve selecting a subject at risk for contracting HIV-1 infection, or a subject at risk of developing AIDS (such as a subject with HIV-1 infection), and administering a disclosed immunogen to the subject to elicit an immune response to HIV-1 in the subject.

Treatment of HIV-1 by inhibiting HIV-1 replication or infection can include delaying the development of AIDS in a subject. Treatment of HIV-1 can also include reducing signs or symptoms associated with the presence of HIV-1 (for example, by reducing or inhibiting HIV-1 replication). In some examples, treatment using the methods disclosed herein prolongs the time of survival of the subject.

In certain embodiments, administering is to the skin, muscle, or buccal cavity. In certain embodiments, administration is by syringe, microneedle, topically, or using pressurized devices, e.g., device comprising a nozzle to push a solution into tissue by means of pressure, e.g., spring-powered without the use of a needle (needle-free devices).

DNA-based vaccines typically use bacterial plasmids to express protein immunogens in vaccinated hosts. Recombinant DNA technology is used to clone cDNAs encoding immunogens of interest into eukaryotic expression plasmids. Vaccine plasmids are then amplified in bacteria, purified, and directly inoculated into the hosts being vaccinated. DNA typically is inoculated by a needle injection of DNA in saline, or by a gene gun device that delivers DNA-coated gold beads into skin. The plasmid DNA is taken up by host cells, the vaccine protein is expressed, processed and presented in the context of self-major histocompatibility (MHC) class I and class II molecules, and an immune response against the DNA-encoded immunogen is generated.

In certain embodiments the present disclosure is a method to generate an immune response against HIV spike protein. Such a response can be a CD8+ T cell immune response or an antibody response. More particularly, the present disclosure relates to "prime and boost" immunization regimes in which the immune response induced by administration of a priming composition is boosted by administration of a boosting composition.

A major protective component of the immune response against a number of pathogens is mediated by T lymphocytes of the CD8+ type, also known as cytotoxic T lymphocytes (CTL). An important function of CD8+ cells is secretion of gamma interferon (IFNγ), and this provides a measure of CD8+ T cell immune response. A second component of the immune response is antibody directed to the proteins of the pathogen.

The present disclosure employs an HIV envelope protein or envelope protein fragment, trimeric complex, or particle as disclosed herein which is found to be an effective means for providing a boost to a CD8+ T cell immune response primed to antigen using any of a variety of different priming compositions and also eliciting an antibody response.

Notably, use of predecessors of the present disclosure allows for an HIV envelope protein or envelope protein fragment, trimeric complex, or particle to boost a CD8+ T cell immune response primed by a DNA vaccine and/or recombinant virus and also eliciting an antibody response. The HIV envelope protein or envelope protein fragment, trimeric complex, or particle disclosed herein may be found to induce a CD8+ T cell response after immunization.

Advantageously, it is contemplated that a vaccination regime using needle-free, intradermal, intramuscular, or mucosal immunization for both prime and boost can be employed, constituting a general immunization regime suitable for inducing CD8+ T cells and also eliciting an antibody response, e.g., in humans. An immune response to an HIV antigen may be primed by immunization with plasmid DNA, recombinant virus, or by infection with an infectious agent.

A further aspect of this disclosure provides a method of inducing a CD8+ T cell immune response to an HIV antigen in an individual, and also eliciting an antibody response, the method comprising administering to the individual a priming composition comprising nucleic acid encoding the HIV envelope proteins or envelope protein fragment, and then administering a boosting composition which comprises an HIV envelope protein or envelope protein fragment, trimeric complex, or particle disclosed herein or nucleic acids encoding the same.

A further aspect provides for use of an HIV envelope protein or envelope protein fragment, trimeric complex, or particle as disclosed herein, in the manufacture of a medicament for administration to a mammal to boost a CD8+ T cell immune response to an HIV antigen, and also eliciting an antibody response. Such a medicament is generally for administration following prior administration of a priming composition comprising nucleic acid and/or recombinant virus encoding the antigen.

The priming composition may comprise DNA encoding the HIV envelope protein or envelope protein fragment disclosed herein, such DNA being in the form of a circular plasmid that is not capable of replicating in mammalian cells. Any selectable marker should preferably not be resistance to an antibiotic used clinically, so for example Kanamycin resistance is preferred to Ampicillin resistance. Antigen expression should be driven by a promoter which is active in mammalian cells, for instance the cytomegalovirus immediate early (CMV IE) promoter.

Pharmaceutical Compositions

In certain embodiments, this disclosure contemplates pharmaceutical compositions containing HIV-1 immunogens e.g., soluble modified HIV envelope proteins, fragments, trimeric complexes or nanoparticles displaying an Env-derived trimer, as well as polynucleotides encoding the proteins described herein for preventing and treating HIV-1 infections. In some embodiments, the immunogens disclosed herein are included in a pharmaceutical composition. The pharmaceutical composition can be either a therapeutic formulation or a prophylactic formulation. Typically, the composition additionally includes one or more pharmaceutically acceptable excipients or carriers and, optionally, other therapeutic ingredients (for example, antibiotics or antiviral drugs). Various pharmaceutically acceptable additives can also be used in the compositions.

For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate. In particular embodiments, suitable for administration to a subject the carrier may be sterile, and/or suspended or otherwise contained in a unit dosage form containing one or more measured doses of the composition suitable to elicit the desired immune response. It may also be accompanied by medications for its use for treatment purposes. The unit dosage form may be, for example, in a sealed vial that contains sterile contents or a syringe for injection into a subject or lyophilized for subsequent solubilization and administration or in a solid or controlled release dosage.

Potential carriers include, but are not limited to, physiologically balanced culture medium, phosphate buffer saline solution, water, emulsions (e.g., oil/water or water/oil emulsions), various types of wetting agents, cryoprotective additives or stabilizers such as proteins, peptides or hydrolysates (e.g., albumin, gelatin), sugars (e.g., sucrose, lactose, sorbitol), amino acids (e.g., sodium glutamate), or other protective agents. The resulting aqueous solutions may be packaged for use as is or lyophilized. Lyophilized preparations are combined with a sterile solution prior to administration for either single or multiple dosing.

Formulated compositions, especially liquid formulations, may contain a bacteriostat to prevent or minimize degradation during storage, including but not limited to effective concentrations of benzyl alcohol, phenol, m-cresol, chlorobutanol, methylparaben, and/or propylparaben. A bacteriostat may be contraindicated for some patients; therefore, a lyophilized formulation may be reconstituted in a solution either containing or not containing such a component.

The pharmaceutical compositions of the disclosure can contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

In certain embodiments, this disclosure contemplates nucleic acids, recombinant vectors, viral vectors, and bacterial plasmids encoding a modified HIV protein or fragment thereof as disclosed herein which form trimeric protein complexes and uses in vaccination methods disclosed herein.

For vaccine compositions, appropriate adjuvants can be additionally included. Examples of suitable adjuvants include, e.g., aluminum hydroxide, lecithin, Freund's adjuvant, MPL™ and IL-12. In some embodiments, the HIV-1 immunogens disclosed herein can be formulated as a controlled-release or time-release formulation. This can be achieved in a composition that contains a slow release polymer or via a microencapsulated delivery system or bioadhesive gel.

The pharmaceutical compositions can be readily employed in a variety of therapeutic or prophylactic applications for treating HIV-1 infection or eliciting an immune response to HIV-1 in a subject. For example, the composition can be administered to a subject to induce an immune response to HIV-1, e.g., to induce production of broadly neutralizing antibodies to HIV-1. For subjects at risk of developing an HIV infection, a vaccine composition can be administered to provide prophylactic protection against viral infection.

Depending on the specific subject and conditions, the pharmaceutical compositions can be administered to subjects by a variety of administration modes known to the person of ordinary skill in the art, for example, intramuscular, subcutaneous, intravenous, intra-arterial, intra-articular, intraperitoneal, or parenteral routes. The appropriate amount of the immunogen can be determined based on the specific disease or condition to be treated or prevented, severity, age of the subject, and other personal attributes of the specific subject (e.g., the general state of the subject's health and the robustness of the subject's immune system). Determination of effective dosages is additionally guided with animal model studies followed up by human clinical trials and is guided by administration protocols that significantly reduce the occurrence or severity of targeted disease symptoms or conditions in the subject.

The pharmaceutical composition can be combined with other agents known in the art for treating or preventing HIV infections. These include, e.g., antibodies or other antiviral agents such as nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir, fosamprenavir, ritonavir, saquinavir, tipranavir, and the like, and fusion protein inhibitors such as enfuvirtide and the like. Administration of the pharmaceutical composition and the known anti-HIV agents can be either concurrently or sequentially.

In certain embodiments, the HIV-1 vaccine immunogens or pharmaceutical compositions can be provided as components of a kit. Optionally, such a kit includes additional components including packaging, instructions and various other reagents, such as buffers, substrates, antibodies or ligands, such as control antibodies or ligands, and detection reagents. An optional instruction sheet can be additionally provided in the kits.

SEQUENCE LISTING

```
<160> NUMBER OF SEQ ID NOS: 12

<210> SEQ ID NO 1
<211> LENGTH: 856
<212> TYPE: PRT
<213> ORGANISM: Artificial
<220> FEATURE:
<223> OTHER INFORMATION: Synthetic construct

<400> SEQUENCE: 1

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
```

```
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460
```

```
Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855
```

<210> SEQ ID NO 2
<211> LENGTH: 8

<212> TYPE: PRT
<213> ORGANISM: Artificial
<220> FEATURE:
<223> OTHER INFORMATION: Synthetic construct

<400> SEQUENCE: 2

Arg Asp Lys Lys Gln Lys Val His
1 5

<210> SEQ ID NO 3
<211> LENGTH: 618
<212> TYPE: PRT
<213> ORGANISM: Artificial
<220> FEATURE:
<223> OTHER INFORMATION: Synthetic construct

<400> SEQUENCE: 3

Met Glu Gly Ser Trp Val Thr Val Tyr Tyr Gly Val Pro Val Trp Lys
1 5 10 15

Glu Ala Lys Thr Thr Leu Phe Cys Ala Ser Asp Ala Lys Ala Tyr Glu
20 25 30

Lys Lys Val His Asn Val Trp Ala Thr His Ala Cys Val Pro Thr Asp
35 40 45

Pro Asn Pro Gln Glu Met Val Leu Ala Asn Val Thr Glu Asn Phe Asn
50 55 60

Met Trp Lys Asn Asp Met Val Glu Gln Met His Glu Asp Ile Ile Ser
65 70 75 80

Leu Trp Asp Glu Ser Leu Lys Pro Cys Val Lys Leu Thr Pro Leu Cys
85 90 95

Val Thr Leu Asn Cys Thr Asn Val Lys Gly Asn Glu Ser Asp Thr Ser
100 105 110

Glu Val Met Lys Asn Cys Ser Phe Asn Ala Thr Thr Glu Leu Arg Asp
115 120 125

Lys Lys Gln Lys Val His Ala Leu Phe Tyr Lys Leu Asp Val Val Pro
130 135 140

Leu Asn Gly Asn Ser Ser Ser Ser Gly Glu Tyr Arg Leu Ile Asn Cys
145 150 155 160

Asn Thr Ser Ala Ile Thr Gln Ala Cys Pro Lys Val Ser Phe Asp Pro
165 170 175

Ile Pro Leu His Tyr Cys Ala Pro Ala Gly Phe Ala Ile Leu Lys Cys
180 185 190

Asn Asn Lys Thr Phe Asn Gly Thr Gly Pro Cys Arg Asn Val Ser Thr
195 200 205

Val Gln Cys Thr His Gly Ile Lys Pro Val Val Ser Thr Gln Leu Leu
210 215 220

Leu Asn Gly Ser Leu Ala Glu Glu Glu Ile Ile Ile Arg Ser Glu Asn
225 230 235 240

Leu Thr Asn Asn Ala Lys Thr Ile Ile Val His Leu Asn Glu Ser Val
245 250 255

Asn Ile Val Cys Thr Arg Pro Asn Asn Asn Thr Arg Lys Ser Ile Arg
260 265 270

Ile Gly Pro Gly Gln Trp Phe Tyr Ala Thr Gly Asp Ile Ile Gly Asn
275 280 285

Ile Arg Gln Ala His Cys Asn Ile Ser Glu Ser Lys Trp Asn Asn Thr
290 295 300

Leu Gln Lys Val Gly Glu Glu Leu Ala Lys His Phe Pro Ser Lys Thr
305 310 315 320

```
Ile Lys Phe Glu Pro Ser Ser Gly Gly Asp Leu Glu Ile Thr Thr His
                325                 330                 335

Ser Phe Asn Cys Arg Gly Glu Phe Phe Tyr Cys Asn Thr Ser Asp Leu
            340                 345                 350

Phe Asn Gly Thr Tyr Arg Asn Gly Thr Tyr Asn His Thr Gly Arg Ser
        355                 360                 365

Ser Asn Gly Thr Ile Thr Leu Gln Cys Lys Ile Lys Gln Ile Ile Asn
    370                 375                 380

Met Trp Gln Glu Val Gly Arg Pro Ile Tyr Ala Pro Pro Ile Glu Gly
385                 390                 395                 400

Glu Ile Thr Cys Asn Ser Asn Ile Thr Gly Leu Leu Leu Leu Arg Asp
                405                 410                 415

Gly Gly Gln Ser Asn Glu Thr Asn Asp Thr Glu Thr Phe Arg Pro Gly
            420                 425                 430

Gly Gly Asp Met Arg Asp Asn Trp Arg Ser Glu Leu Tyr Lys Tyr Lys
        435                 440                 445

Val Val Glu Ile Lys Pro Leu Gly Val Ala Pro Thr Glu Ala Lys Arg
    450                 455                 460

Arg Val Val Glu Gly Gly Gly Gly Ser Gly Gly Gly Gly Ser Ala Val
465                 470                 475                 480

Gly Ile Gly Ala Val Phe Leu Gly Phe Leu Gly Ala Ala Gly Ser Thr
                485                 490                 495

Met Gly Ala Ala Ser Met Thr Leu Thr Val Gln Ala Arg Gln Leu Leu
            500                 505                 510

Ser Gly Asn Pro Asp Trp Leu Pro Asp Met Thr Val Trp Gly Ile Lys
        515                 520                 525

Gln Leu Gln Ala Arg Val Leu Ala Ile Glu Arg Tyr Leu Lys Asp Gln
    530                 535                 540

Gln Leu Leu Gly Met Trp Gly Cys Ser Gly Lys Leu Ile Cys Thr Thr
545                 550                 555                 560

Ala Val Pro Trp Asn Ser Ser Trp Ser Asn Lys Ser Gln Asn Glu Ile
                565                 570                 575

Trp Gly Asn Met Thr Trp Met Gln Trp Asp Arg Glu Ile Asn Asn Tyr
            580                 585                 590

Thr Asn Thr Ile Tyr Arg Leu Leu Glu Asp Ser Gln Asn Gln Gln Glu
        595                 600                 605

Lys Asn Glu Lys Asp Leu Leu Ala Leu Asp
    610                 615
```

<210> SEQ ID NO 4
<211> LENGTH: 8
<212> TYPE: PRT
<213> ORGANISM: Artificial
<220> FEATURE:
<223> OTHER INFORMATION: Synthetic construct

<400> SEQUENCE: 4

```
Arg Asp Lys Lys Gln Lys Val Tyr
1               5
```

<210> SEQ ID NO 5
<211> LENGTH: 618
<212> TYPE: PRT
<213> ORGANISM: Artificial
<220> FEATURE:
<223> OTHER INFORMATION: Synthetic construct

<400> SEQUENCE: 5

```
Met Glu Gly Ser Trp Val Thr Val Tyr Tyr Gly Val Pro Val Trp Lys
1               5                   10                  15

Glu Ala Lys Thr Thr Leu Phe Cys Ala Ser Asp Ala Lys Ala Tyr Glu
            20                  25                  30

Lys Lys Val His Asn Val Trp Ala Thr His Ala Cys Val Pro Thr Asp
        35                  40                  45

Pro Asn Pro Gln Glu Met Val Leu Ala Asn Val Thr Glu Asn Phe Asn
    50                  55                  60

Met Trp Lys Asn Asp Met Val Glu Gln Met His Glu Asp Ile Ile Ser
65                  70                  75                  80

Leu Trp Asp Glu Ser Leu Lys Pro Cys Val Lys Leu Thr Pro Leu Cys
                85                  90                  95

Val Thr Leu Asn Cys Thr Asn Val Lys Gly Asn Glu Ser Asp Thr Ser
            100                 105                 110

Glu Val Met Lys Asn Cys Ser Phe Asn Ala Thr Thr Glu Leu Arg Asp
        115                 120                 125

Lys Lys Gln Lys Val Tyr Ala Leu Phe Tyr Lys Leu Asp Val Val Pro
    130                 135                 140

Leu Asn Gly Asn Ser Ser Ser Ser Gly Glu Tyr Arg Leu Ile Asn Cys
145                 150                 155                 160

Asn Thr Ser Ala Ile Thr Gln Ala Cys Pro Lys Val Ser Phe Asp Pro
                165                 170                 175

Ile Pro Leu His Tyr Cys Ala Pro Ala Gly Phe Ala Ile Leu Lys Cys
            180                 185                 190

Asn Asn Lys Thr Phe Asn Gly Thr Gly Pro Cys Arg Asn Val Ser Thr
        195                 200                 205

Val Gln Cys Thr His Gly Ile Lys Pro Val Val Ser Thr Gln Leu Leu
    210                 215                 220

Leu Asn Gly Ser Leu Ala Glu Glu Glu Ile Ile Ile Arg Ser Glu Asn
225                 230                 235                 240

Leu Thr Asn Asn Ala Lys Thr Ile Ile Val His Leu Asn Glu Ser Val
                245                 250                 255

Asn Ile Val Cys Thr Arg Pro Asn Asn Asn Thr Arg Lys Ser Ile Arg
            260                 265                 270

Ile Gly Pro Gly Gln Trp Phe Tyr Ala Thr Gly Asp Ile Ile Gly Asn
        275                 280                 285

Ile Arg Gln Ala His Cys Asn Ile Ser Glu Ser Lys Trp Asn Asn Thr
    290                 295                 300

Leu Gln Lys Val Gly Glu Glu Leu Ala Lys His Phe Pro Ser Lys Thr
305                 310                 315                 320

Ile Lys Phe Glu Pro Ser Ser Gly Gly Asp Leu Glu Ile Thr Thr His
                325                 330                 335

Ser Phe Asn Cys Arg Gly Glu Phe Phe Tyr Cys Asn Thr Ser Asp Leu
            340                 345                 350

Phe Asn Gly Thr Tyr Arg Asn Gly Thr Tyr Asn His Thr Gly Arg Ser
        355                 360                 365

Ser Asn Gly Thr Ile Thr Leu Gln Cys Lys Ile Lys Gln Ile Ile Asn
    370                 375                 380

Met Trp Gln Glu Val Gly Arg Pro Ile Tyr Ala Pro Pro Ile Glu Gly
385                 390                 395                 400

Glu Ile Thr Cys Asn Ser Asn Ile Thr Gly Leu Leu Leu Leu Arg Asp
                405                 410                 415
```

```
Gly Gly Gln Ser Asn Glu Thr Asn Asp Thr Glu Thr Phe Arg Pro Gly
            420                 425                 430

Gly Gly Asp Met Arg Asp Asn Trp Arg Ser Glu Leu Tyr Lys Tyr Lys
        435                 440                 445

Val Val Glu Ile Lys Pro Leu Gly Val Ala Pro Thr Glu Ala Lys Arg
    450                 455                 460

Arg Val Val Glu Gly Gly Gly Gly Ser Gly Gly Gly Gly Ser Ala Val
465                 470                 475                 480

Gly Ile Gly Ala Val Phe Leu Gly Phe Leu Gly Ala Ala Gly Ser Thr
                485                 490                 495

Met Gly Ala Ala Ser Met Thr Leu Thr Val Gln Ala Arg Gln Leu Leu
            500                 505                 510

Ser Gly Asn Pro Asp Trp Leu Pro Asp Met Thr Val Trp Gly Ile Lys
        515                 520                 525

Gln Leu Gln Ala Arg Val Leu Ala Ile Glu Arg Tyr Leu Lys Asp Gln
    530                 535                 540

Gln Leu Leu Gly Met Trp Gly Cys Ser Gly Lys Leu Ile Cys Thr Thr
545                 550                 555                 560

Ala Val Pro Trp Asn Ser Ser Trp Ser Asn Lys Ser Gln Asn Glu Ile
                565                 570                 575

Trp Gly Asn Met Thr Trp Met Gln Trp Asp Arg Glu Ile Asn Asn Tyr
            580                 585                 590

Thr Asn Thr Ile Tyr Arg Leu Leu Glu Asp Ser Gln Asn Gln Gln Glu
        595                 600                 605

Lys Asn Glu Lys Asp Leu Leu Ala Leu Asp
    610                 615


<210> SEQ ID NO 6
<211> LENGTH: 10
<212> TYPE: PRT
<213> ORGANISM: Artificial
<220> FEATURE:
<223> OTHER INFORMATION: Synthetic construct

<400> SEQUENCE: 6

Gly Gly Gly Gly Ser Gly Gly Gly Gly Ser
1               5                   10


<210> SEQ ID NO 7
<211> LENGTH: 4
<212> TYPE: PRT
<213> ORGANISM: Artificial
<220> FEATURE:
<223> OTHER INFORMATION: Synthetic construct

<400> SEQUENCE: 7

Arg Glu Lys Arg
1


<210> SEQ ID NO 8
<211> LENGTH: 6
<212> TYPE: PRT
<213> ORGANISM: Artificial
<220> FEATURE:
<223> OTHER INFORMATION: Synthetic construct

<400> SEQUENCE: 8

Arg Arg Arg Arg Arg Arg
1               5
```

-continued

```
<210> SEQ ID NO 9
<211> LENGTH: 6
<212> TYPE: PRT
<213> ORGANISM: Artificial
<220> FEATURE:
<223> OTHER INFORMATION: Synthetic construct

<400> SEQUENCE: 9

Gly Gly Gly Gly Gly Gly
1               5


<210> SEQ ID NO 10
<211> LENGTH: 5
<212> TYPE: PRT
<213> ORGANISM: Artificial
<220> FEATURE:
<223> OTHER INFORMATION: Synthetic construct

<400> SEQUENCE: 10

Gly Gly Gly Gly Thr
1               5


<210> SEQ ID NO 11
<211> LENGTH: 6
<212> TYPE: PRT
<213> ORGANISM: Artificial
<220> FEATURE:
<223> OTHER INFORMATION: Synthetic construct

<400> SEQUENCE: 11

Gly Gly Gly Pro Pro Pro
1               5


<210> SEQ ID NO 12
<211> LENGTH: 7
<212> TYPE: PRT
<213> ORGANISM: Artificial
<220> FEATURE:
<223> OTHER INFORMATION: Synthetic construct

<400> SEQUENCE: 12

Gly Gly Gly Ala Pro Pro Pro
1               5
```

What is claimed is:

1. A non-naturally occurring HIV envelope protein or envelope protein fragment capable of forming a trimeric complex comprising the amino acid sequence of (SEQ ID NO: 3)

MEGSWVTVYYGVPVWKEAKTTLFCASDAKAYEKKVHNVWATHACVPTDP

NPQEMVLANVTENFNMWKNDMVEQMHEDIISLWDESLKPCVKLTPLCVT

LNCTNVKGNESDTSEVMKNCSFNATTELRDKKQKVHALFYKLDVVPLNG

NSSSSGEYRLINCNTSAITQACPKVSFDPIPLHYCAPAGFAILKCNNKT

FNGTGPCRNVSTVQCTHGIKPVVSTQLLLNGSLAEEEIIIRSENLTNNA

KTIIVHLNESVNIVCTRPNNNTRKSIRIGPGQWFYATGDIIGNIRQAHC

NISESKWNNTLQKVGEELAKHFPSKTIKFEPSSGGDLEITTHSFNCRGE

FFYCNTSDLFNGTYRNGTYNHTGRSSNGTITLQCKIKQIINMWQEVGRP

IYAPPIEGEITCNSNITGLLLLRDGGQSNETNDTETFRPGGGDMRDNWR

-continued

SELYKYKVVEIKPLGVAPTEAKRRVVEGGGGSGGGGSAVGIGAVFLGFL

GAAGSTMGAASMTLTVQARQLLSGNPDWLPDMTVWGIKQLQARVLAIER

YLKDQQLLGMWGCSGKLICTTAVPWNSSWSNKSQNEIWGNMTWMQWDRE

INNYTNTIYRLLEDSQNQQEKNEKDLLALD, or variant having greater than 80% sequence identity.

2. The protein of claim 1, which is non-naturally occurring because the envelope protein or envelope protein fragment contains one or more amino acids substituted with cysteine (C).

3. The protein of claim 1, which is non-naturally occurring because the envelope protein or envelope protein fragment contains a linker comprising polyglycine sequence between a gp120 domain or fragment thereof and a gp41 domain or fragment thereof.

4. The protein of claim 1, comprising the amino acid sequence of RDKKQKVH (SEQ ID NO: 2).

5. The protein of claim 1, wherein position 127 is arginine (R), position 131 is glutamine (Q), and position 134 is histidine (H) relative to SEQ ID NO: 3, wherein the N-terminal methionine (M) is position 39.

6. A trimeric protein complex comprising the peptide of claim 1.

7. A nucleic acid encoding the protein of claim 1.

8. A vector comprising a nucleic acid of claim 7 in operable combination with a heterologous promoter.

9. An expression system comprising a vector of claim 8.

10. A virus like particle comprising a protein of claim 1.

11. A pharmaceutical composition comprising a protein of claim 1, a trimeric protein complex comprising the protein, or a vector encoding the same and a pharmaceutically acceptable excipient.

12. A method of vaccinating for HIV-1 comprising administering an effective amount of a protein of claim 1, a trimeric protein complex comprising the protein, or a vector encoding the protein to a subject.

13. A method of treating a subject with an HIV infection comprising administering an effective amount of a protein of claim 1, a trimeric protein complex comprising the protein, or a vector encoding the protein to a subject in need thereof.

14. The method of claim 13, wherein the protein, trimeric protein complex, or vector encoding the protein is administered in combination with an adjuvant.

15. The method of claim 13, wherein the protein, trimeric protein complex, or vector encoding the protein is administered in combination with an antiviral agent.

* * * * *